US010267810B2

(12) United States Patent
Clarke et al.

(10) Patent No.: US 10,267,810 B2
(45) Date of Patent: *Apr. 23, 2019

(54) METHODS FOR DETECTING VITAMIN D METABOLITES BY MASS SPECTROMETRY

(71) Applicant: Quest Diagnostics Investments Incorporated, Wilmington, DE (US)

(72) Inventors: Nigel J. Clarke, Vista, CA (US); Brett Holmquist, Mission Viejo, CA (US); Gloria Kwang-Ja Lee, Irvine, CA (US); Richard E. Reitz, Las Vegas, NV (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/848,325

(22) Filed: Dec. 20, 2017

(65) Prior Publication Data

US 2018/0156828 A1 Jun. 7, 2018

Related U.S. Application Data

(63) Continuation of application No. 15/388,844, filed on Dec. 22, 2016, now Pat. No. 9,880,180, which is a continuation of application No. 15/005,801, filed on Jan. 25, 2016, now Pat. No. 9,529,004, which is a continuation of application No. 14/180,722, filed on Feb. 14, 2014, now Pat. No. 9,244,084, which is a continuation of application No. 13/871,457, filed on Apr. 26, 2013, now Pat. No. 8,936,943, which is a continuation of application No. 13/327,650, filed on Dec. 15, 2011, now Pat. No. 8,431,411, which is a continuation of application No. 13/115,916, filed on May 25, 2011, now Pat. No. 8,101,427, which is a continuation of application No. 11/386,215, filed on Mar. 21, 2006, now Pat. No. 7,972,867, which is a continuation-in-part of application No. 11/101,166, filed on Apr. 6, 2005, now Pat. No. 7,745,226.

(51) Int. Cl.
*G01N 33/82* (2006.01)
*G01N 30/72* (2006.01)
*G01N 30/88* (2006.01)
*H01J 49/00* (2006.01)
*H01L 49/00* (2006.01)

(52) U.S. Cl.
CPC ......... *G01N 33/82* (2013.01); *G01N 30/7233* (2013.01); *G01N 30/72* (2013.01); *G01N 2030/8813* (2013.01); *G01N 2030/8822* (2013.01); *G01N 2458/15* (2013.01); *G01N 2560/00* (2013.01); *H01J 49/00* (2013.01); *H01J 49/004* (2013.01); *Y10T 436/20* (2015.01); *Y10T 436/203332* (2015.01); *Y10T 436/24* (2015.01)

(58) Field of Classification Search
CPC ... G01N 2030/8813; G01N 2030/8822; G01N 2458/15; G01N 2560/00; G01N 30/72; G01N 30/7233; G01N 33/82; H01J 40/00; H01J 40/004; Y10T 436/20; Y10T 436/203332; Y10T 436/24
USPC .......................... 436/131, 173; 250/281, 282
See application file for complete search history.

(56) References Cited

U.S. PATENT DOCUMENTS

| | | |
|---|---|---|
| 4,332,591 A | 6/1982 | Oi et al. |
| 5,614,408 A | 3/1997 | Stanker et al. |
| 5,772,874 A | 6/1998 | Quinn et al. |
| 5,795,469 A | 8/1998 | Quinn et al. |
| 5,916,523 A | 6/1999 | Yan et al. |
| 5,919,368 A | 7/1999 | Quinn et al. |
| 5,968,367 A | 10/1999 | Quinn et al. |
| 6,107,623 A | 8/2000 | Bateman et al. |
| 6,124,137 A | 9/2000 | Hutchens et al. |
| 6,204,500 B1 | 3/2001 | Whitehouse et al. |
| 6,228,853 B1 | 5/2001 | Dowle et al. |
| 6,268,144 B1 | 7/2001 | Koester |
| 6,787,660 B1 | 9/2004 | Armbruster et al. |
| 6,977,143 B1 | 12/2005 | Caulfield et al. |
| 7,019,146 B1 | 3/2006 | Ishigai et al. |
| 7,087,395 B1 | 8/2006 | Garrity et al. |
| 7,321,116 B2 | 1/2008 | Picard et al. |
| 7,348,137 B2 | 3/2008 | Caulfield et al. |
| 7,473,560 B2 | 1/2009 | Soldin |
| 7,482,162 B2 | 1/2009 | Laurie et al. |
| 7,618,827 B2 | 11/2009 | Soldin |
| 7,700,365 B2 | 4/2010 | Singh et al. |

(Continued)

FOREIGN PATENT DOCUMENTS

| | | |
|---|---|---|
| CN | 1993134 A | 7/2007 |
| JP | H04505468 A | 9/1992 |

(Continued)

OTHER PUBLICATIONS

Non-Final Office Action dated Sep. 19, 2014 for U.S. Appl. No. 14/180,722, filed Feb. 14, 2014.

(Continued)

*Primary Examiner* — Maureen Wallenhorst
(74) *Attorney, Agent, or Firm* — Quest Diagnostics, Inc.

(57) ABSTRACT

Provided are methods of detecting the presence or amount of a vitamin D metabolite in a sample using mass spectrometry. The methods generally directed to ionizing a vitamin D metabolite in a sample and detecting the amount of the ion to determine the presence or amount of the vitamin D metabolite in the sample. Also provided are methods to detect the presence or amount of two or more vitamin D metabolites in a single assay.

16 Claims, 4 Drawing Sheets

(56) References Cited

U.S. PATENT DOCUMENTS

| | | | |
|---|---|---|---|
| 7,745,226 | B2 | 6/2010 | Clarke et al. |
| 7,972,867 | B2 | 7/2011 | Clarke et al. |
| 7,972,868 | B2 | 7/2011 | Holmquist et al. |
| 7,977,117 | B2 | 7/2011 | Holmquist et al. |
| 8,034,627 | B2 | 10/2011 | Holmquist et al. |
| 8,076,157 | B2 | 12/2011 | Holmquist et al. |
| 8,084,269 | B2 | 12/2011 | Holmquist et al. |
| 8,101,427 | B2 | 1/2012 | Clarke et al. |
| 8,173,442 | B2 | 5/2012 | Holmquist et al. |
| 8,431,411 | B2 | 4/2013 | Clarke et al. |
| 8,936,943 | B2 | 1/2015 | Clarke et al. |
| 9,244,084 | B2 | 1/2016 | Clarke et al. |
| 9,529,004 | B2 | 12/2016 | Clarke et al. |
| 9,535,077 | B2 | 1/2017 | Holmquist et al. |
| 9,880,180 | B2 * | 1/2018 | Clarke ............... G01N 33/82 |
| 2003/0171605 | A1 | 9/2003 | Reddy et al. |
| 2004/0235193 | A1 | 11/2004 | Soldin |
| 2006/0054807 | A1 | 3/2006 | Picard et al. |
| 2006/0094125 | A1 | 5/2006 | Singh et al. |
| 2006/0228808 | A1 | 10/2006 | Clarke et al. |
| 2006/0228809 | A1 | 10/2006 | Clarke et al. |
| 2006/0236886 | A1 | 10/2006 | Leenders et al. |
| 2006/0263886 | A1 | 11/2006 | Peters et al. |
| 2007/0037286 | A1 | 2/2007 | Purkayastha |
| 2007/0139956 | A1 | 6/2007 | Sugimoto et al. |
| 2008/0128606 | A1 | 6/2008 | Grant et al. |
| 2008/0241955 | A1 | 10/2008 | Purkayastha et al. |
| 2008/0287661 | A1 | 11/2008 | Jones |
| 2009/0137056 | A1 | 5/2009 | Holmquist et al. |
| 2011/0133068 | A1 | 6/2011 | Holmquist et al. |
| 2011/0212534 | A1 | 9/2011 | Taylor et al. |
| 2011/0226944 | A1 | 9/2011 | Holmquist et al. |
| 2011/0301063 | A1 | 12/2011 | Netzel et al. |
| 2012/0061562 | A1 | 3/2012 | Holmquist et al. |
| 2014/0127825 | A1 | 5/2014 | Dey et al. |
| 2014/0147878 | A1 | 5/2014 | Herman et al. |
| 2014/0234989 | A1 | 8/2014 | Holmquist et al. |

FOREIGN PATENT DOCUMENTS

| | | |
|---|---|---|
| JP | H06341980 A | 12/1994 |
| JP | H0727763 A | 1/1995 |
| JP | 2002518474 A | 6/2002 |
| JP | 2004515763 A | 5/2004 |
| JP | 2005503534 A | 2/2005 |
| JP | 2007515625 A | 6/2007 |
| JP | 2009115724 A | 5/2009 |
| JP | 2009543069 A | 12/2009 |
| JP | 2011505014 | 2/2011 |
| WO | 9112239 A1 | 8/1991 |
| WO | 9533279 A1 | 12/1995 |
| WO | 9618618 A1 | 6/1996 |
| WO | 9967211 A1 | 12/1999 |
| WO | 0246746 A2 | 6/2002 |
| WO | 02057797 A2 | 7/2002 |
| WO | 2004002996 A1 | 1/2004 |
| WO | 2006034427 A2 | 3/2006 |
| WO | 2006107339 A2 | 10/2006 |
| WO | 2006107814 A2 | 10/2006 |
| WO | 2007039193 A1 | 4/2007 |
| WO | 2007139956 A2 | 12/2007 |
| WO | 2008005846 A2 | 1/2008 |
| WO | 2008097246 A2 | 8/2008 |
| WO | 2008156139 A1 | 12/2008 |
| WO | 2009070594 A1 | 6/2009 |

OTHER PUBLICATIONS

Non-Final Office Action dated Sep. 19, 2016 for U.S. Appl. No. 14/267,014, filed May 1, 2014.
Non-Final Office Action dated Dec. 20, 2011 for U.S. Appl. No. 13/299,212, filed Nov. 17, 2011.
Non-Final Office Action dated Jun. 20, 2013 for U.S. Appl. No. 13/514,892, filed Jun. 8, 2012.
Non-Final Office Action dated Sep. 20, 2012 for U.S. Appl. No. 13/287,012, filed Nov. 1, 2011.
Non-Final Office Action dated Jul. 21, 2011 for U.S. Appl. No. 13/165,685, filed Jun. 21, 2011.
Non-Final Office Action dated Aug. 22, 2014 for U.S. Appl. No. 13/514,892, filed Jun. 8, 2012.
Non-Final Office Action dated Jan. 22, 2016 for U.S. Appl. No. 14/063,956, filed Oct. 25, 2013.
Non-Final Office Action dated Apr. 23, 2012 for U.S. Appl. No. 13/287,012, filed Nov. 1, 2011.
Non-Final Office Action dated Jun. 24, 2010 for U.S. Appl. No. 11/946,765, filed Nov. 28, 2007.
Non-Final Office Action dated Mar. 24, 2016 for U.S. Appl. No. 15/005,801, filed Jan. 25, 2016.
Non-Final Office Action dated Jun. 26, 2012 for U.S. Appl. No. 13/436,651, filed Mar. 30, 2012.
Non-Final Office Action dated Jun. 28, 2010 for U.S. Appl. No. 12/630,790, filed Dec. 3, 2009.
Non-Final Office Action dated Jul. 29, 2011 for U.S. Appl. No. 13/117,997, filed May 27, 2011.
Non-Final Office Action dated Jun. 29, 2011 for U.S. Appl. No. 13/115,935, filed May 25, 2011.
Non-Final Office Action dated Jun. 25, 2015 for U.S. Appl. No. 14/639,834, filed Mar. 5, 2015.
Odrzywolska M., et al., "Convergent Synthesis, Chiral HPLC, and Vitamin D Receptor Affinity of Analogs of 1,25-Dihydroxycholecalciferol," Chirality, 1999, vol. 11 (3), pp. 249-255.
Office Action dated May 30, 2017 for Japanese Application No. 2013-047593 filed Mar. 11, 2013.
Patent Board Decision—Examiner Affirmed mailed Apr. 25, 2016 for U.S. Appl. No. 12/964,717, filed Dec. 9, 2010.
Polson C., et al., "Optimization of Protein Precipitation Based Upon Effectiveness of Protein Removal and Ionization Effect in Liquid Chromatography-Tandem Mass Spectrometry," Journal of Chromatography B, 2003, vol. 785 (2), pp. 263-275.
Robb D.B., et al., "Atmospheric Pressure Photoionization: An Ionization Method for Liquid Chromatography-Mass Spectrometry," Analytical Chemistry, 2000, vol. 72 (15), pp. 3653-3659.
Roussis S.G., et al., "Quantitative Determination of Polar and Ionic Compounds in Petroleum Fractions by Atmospheric Pressure Chemical Ionization and Electrospray Ionization Mass Spectrometry," Rapid Communication in Mass Spectrometry, 2002, vol. 16 (13), pp. 1295-1303.
Salm P., et al., "The Quantification of Sirolimus by High-Performance Liquid Chromatography-Tandem Mass Spectrometry and Microparticle Enzyme Immunoassay in Renal Transplant Recipients," Clinical Therapeutics, 2000, vol. 22 Suppl B, pp. B71-B85.
Singh F.J., et al., "C-3 Epimers Can Account for a Significant Proportion of Total Circulating 25-Hydroxyvitamin D in Infants, Complicating Accurate Measurement and Interpretation of Vitamin D Status," The Journal of Clinical Endocrinology & Metabolism, 2006, vol. 91 (8), pp. 3055-3061.
Supplementary European Search Report for Application No. EP06749272, dated Feb. 2, 2009, 7 pages.
Supplementary European Search Report for Application No. EP10836711, dated Oct. 28, 2013, 11 pages.
Supplementary European Search Report for Application No. EP11184151, dated Dec. 1, 2011, 7 pages.
Taylor P.J., et al., "Simultaneous Quantification of Tacrolimus and Sirolimus in Human Blood, by High-Performance Liquid Chromatography-Tandem Mass Spectrometry," Therapeutic Drug Monitoring, 2000, vol. 22 (5), pp. 608-612.
Tsugawa N., et al., "Determination of 25-Hydroxyvitamin D in Human Plasma Using High-Performance Liquid Chromatography-Tandem Mass Spectrometry," Analytical Chemistry, 2005, vol. 77 (9), pp. 3001-3007.
Vieth R., et al., "Age-Related Changes in the 25-Hydroxyvitamin D Versus Parathyroid Hormone Relationship Suggest a Different Reason Why Older Adults Require More Vitamin D," Journal of Clinical Endocrinology and Metabolism, 2003, vol. 88 (1), pp. 185-191.

(56) References Cited

OTHER PUBLICATIONS

Vieth R., "Vitamin D Supplementation, 25-Hydroxyvitamin D Concentrations, and Safety," The American Journal of Clinical Nutrition, 1999, vol. 69 (5), pp. 842-856.

Vogeser M., et al., "Candidate Reference Method for the Quantification of Circulating 25-Hydroxyvitamin D3 by Liquid Chromatography-Tandem Mass Spectrometry," Clinical Chemistry, 2004, vol. 50 (8), pp. 1415-1417.

Vreeken R.J., et al., "On-Line Post-Column Diels-Alder Derivatization for the Determination of Vitamin D3 and Its Metabolites by Liquid Chromatography/Thermospray Mass Spectrometry," Biological Mass Spectrometry, 1993, vol. 22 (11), pp. 621-632.

Wang K., et al., "An Electron-Capture Dienophile Derivatization Agent for Increasing Sensitivity: Determination of a Vitamin D Analog (Ro 24-2090) in Plasma Sample with Liquid Chromatography/Mass Spectrometry," Analytical Biochemistry, 1996, vol. 243 (1), pp. 28-40.

Watson D., et al., "Analysis of Vitamin D and Its Metabolites Using Thermospray Liquid Chromatography/Mass Spectrometry," Biomedical Chromatography, 1991, vol. 5 (4), pp. 153-160.

Weiskopf A.S., et al., "Examination of Structurally Selective Derivatization of Vitamin D3 Analogues by Electrospray Mass Spectrometry," Journal of Mass Spectrometry, 2001, vol. 36 (1), pp. 71-78.

Wharton B., et al., "Rickets," The Lancet, 2003, vol. 362 (9393), pp. 1389-1400.

Wright Jr., G.L., et al., "Proteinchip Surface Enhanced Laser Desorption/Ionization (SELDI) Mass Spectrometry: A Novel Protein Biochip Technology for Detection of Prostate Cancer Biomarkers in Complex Protein Mixtures," Prostate Cancer and Prostatic Diseases, 1999, vol. 2 (5-6), pp. 264-276.

Written Opinion for Application No. PCT/US06/12539, dated Jan. 4, 2007, 3 Pages.

Written Opinion for Application No. PCT/US08/84709, dated Feb. 24, 2009, 9 Pages.

Written Opinion for Application No. PCT/US10/59771, dated Feb. 11, 2011, 4 Pages.

Yeung B., et al., "Characterization of the Metabolic Pathway of 1,25-Dihydroxy-16-Ene Vitamin D3 in Rat Kidney by On-Line High Performance Liquid Chromatography-Electrospray Tandem Mass Spectrometry," Biochemical Pharmacology, 1995, vol. 49 (8), pp. 1099-1110.

Yeung B., et al., "Characterization of Viatmin D.Sub.3 Metabolites Using Continuous-Flow Fast Atom Bombardment Tandem Mass Spectrometry and High Performance Liquid Chromatography," Chromatographia, 1993, vol. 645 (1), pp. 115-123.

Yeung B., et al., "Role of Mass Spectrometry in Vitamin D Research," Mass Spectrometry Reviews, 1995, vol. 14 (3), pp. 179-194.

Zimmer D., et al., "Comparison of Turbulent-Flow Chromatography with Automated Solid-Phase Extraction in 96-Well Plates and Liquid-Liquid Extraction Used as Plasma Sample Preparation Techniques for Liquid Chromatography-Tandem Mass Spectrometry," Journal of Chromatography A, 1999, vol. 854, pp. 23-35.

Aberhart D. J., et al., "Studies on the Adduct of 4-Phenyl-1,2,4-Triazoline-3,5-Dione with Vitamin D3," Journal of Organic Chemistry, 1976, vol. 41 (12), pp. 2098-2102.

Adachi T., et al., "Determination of Vitamin D3 nad D2 in the Multi-Vitamin Tablets by High-Performance Liquid Chromatography/Atmospheric Pressure Chemical Ionization Mass Spectrometry," Analytical Science, 1994, vol. 10, pp. 457-460.

Aguera A., et al., "One-Year Routine Application of a New Method Based on Liquid Chromatography-Tandem Mass Spectrometry to the Analysis of 16 Multiclass Pesticides in Vegetable Samples," Journal of Chromatography A, 2004, vol. 1045 (1-2), pp. 125-135.

Armas L.A., et al., "Vitamin D2 is Much Less Effective than Vitamin D3 in Humans," The Journal of Clinical Endocrinology & Metabolism, 2004, vol. 89 (11), pp. 5387-5391.

Aronov P.A., et al., "Metabolic Profiling of Major Vitamin D Metabolites Using Diels-Alder Derivatization and Ultra-Performance Liquid Chromatography-Tandem Mass Spectrometry," Analytical and Bioanalytical Chemistry, 2008, vol. 391 (5), pp. 1917-1930.

Ascalone V., et al., "Stereospecific Determination of Amisulpride, a New Benzamide Derivative, In Human Plasma and Urine by Automated Solid-Phase Extraction and Liquid Chromatography on a Chiral Column Application to Pharmacokinetics," Journal of Chromatography B, 1996, vol. 676, pp. 95-105.

Bartolucci G., et al., "Liquid Chromatography Tandem Mass Spectrometric Quantitation of Sulfamethazine and its Metabolites: Direct Analysis of Swine Urine by Triple Quadrupole and by Ion Trap Mass Spectrometry," Rapid Communications in Mass Spectrometry, 2000, vol. 14 (11), pp. 967-973.

Boyer F.O., et al., "Determination of Vitamins D2, D3, K1 and K3 and Some Hydroxy Metabolites of Vitamin D3 in Plasma Using a Continuous Clean-Up-Preconcentration Procedure Coupled On-Line with Liquid Chromatography-UV Detection," Analyst, 1999, vol. 124 (3), pp. 401-406.

Bunch D.R., et al., "Development and Validation of a Liquid Chromatography-Tandem Mass Spectrometry Assay for Serum 25-Hydroxyvitamin D2/D3 Using a Turbulent Flow Online Extraction Technology," Clinical Chemistry and Laboratory Medicine, 2009, vol. 47 (12), pp. 1565-1572.

Busch K.L., et al., "A Glossary for Mass Spectrometry," Mass Spectrometry, 2002, vol. 17 (65), pp. 526-534.

Capote P.F., et al., "Identification and Determination of Fat-Soluble Vitamins and Metabolites in Human Serum by Liquid Chromatography/Triple Quadrupole Mass Spectrometry with Multiple Reaction Monitoring," Rapid Communications in Mass Spectrometry, 2007, vol. 21 (11), pp. 1745-1754.

Chen W.J., et al., "Induction of Apoptosis by Vitamin D2, Ergocalciferol, via Reactive Oxygen Generation, Glutathione Depletion, and Caspase Activation in Human Leukemia Cells," Journal of Food and Chemistry, 2008, vol. 56 (9), pp. 2996-3005.

Coldwell R.D., et al., "Mass Fragmentographic Assay for 25-Hydroxyvitamin D in Plasma Without Derivatization: Enhanced Sensitivity for Metabolites of Vitamins D2 and D3 After Pre-column Dehydration," Journal of Mass Spectrometry, 1995, vol. 30 (2), pp. 348-356.

Coldwell R.D., et al., "Measurement of Vitamins D2 and D3 and Seven Major Metabolites in a Single Sample of Human Plasma Using Gas Chromatography/Mass Spectrometry," Biomedical and Environmental Mass Spectrometry, 1988, vol. 16 (1-12), pp. 81-85.

Coldwell R.D., et al., "Stable Isotope-Labeled Vitamin D, Metabolites and Chemical Analogs: Synthesis and Use in Mass Spectrometric Studies," Steroids, 1990, vol. 55 (10), pp. 418-432.

Examiner's Answer to Appeal Brief mailed Jan. 9, 2014 for U.S. Appl. No. 12/964,717, filed Dec. 9, 2010.

Examiner's Answer to Appeal Brief mailed Sep. 20, 2016 for U.S. Appl. No. 12/964,710, filed Dec. 9, 2010.

Extended European Search Report for Application No. 06749272.8, dated Feb. 2, 2009.

Extended European Search Report for Application No. 08853843.4, dated Dec. 22, 2010.

Extended European Search Report for Application No. 10836702.0, dated Oct. 2, 2013.

Extended European Search Report for Application No. 10836711.1, dated Nov. 14, 2013.

Extended European Search Report for Application No. 11184151.6, dated Dec. 1, 2011.

Extended European Search Report for Application No. 16154623.9, dated Apr. 12, 2016.

Fiehn O., et al., "Mass Spectrometry: Quantitation" In: D Ganten and K Ruckpaul (Editors): "Encyclopedic Reference of Genomics and Proteomics in Molecular Medicine", Springer, 2006, pp. 1030-1034.

Final Office Action dated Oct. 2, 2013 for U.S. Appl. No. 13/751,915, filed Jan. 28, 2013.

Final Office Action dated May 4, 2015 for U.S. Appl. No. 12/964,710, filed Dec. 9, 2010.

Final Office Action dated Jan. 6, 2011 for U.S. Appl. No. 12/630,790, filed Dec. 3, 2009.

(56) References Cited

OTHER PUBLICATIONS

Final Office Action dated Jun. 8, 2017 for U.S. Appl. No. 14/267,014, filed May 1, 2014.
Final Office Action dated Apr. 9, 2015 for U.S. Appl. No. 14/180,722, filed Feb. 14, 2014.
Final Office Action dated Sep. 12, 2012 for U.S. Appl. No. 13/327,650, filed Dec. 15, 2011.
Final Office Action dated Dec. 13, 2013 for U.S. Appl. No. 13/514,892, filed Jun. 8, 2012.
Final Office Action dated Dec. 17, 2010 for U.S. Appl. No. 11/946,765, filed Nov. 28, 2007.
Final Office Action dated Dec. 17, 2010 for U.S. Appl. No. 12/630,796, filed Dec. 3, 2009.
Final Office Action dated Jun. 27, 2013 for U.S. Appl. No. 12/964,717, filed Dec. 9, 2010.
Final Office Action dated Feb. 28, 2013 for U.S. Appl. No. 12/964,710, filed Dec. 9, 2010.
Gao S., et al., "Sensitivity Enhancement in Liquid Chromatography/Atmospheric Pressure Ionization Mass Spectrometry Using Derivatization and Mobile Phase Additives," Journal of Chromatography B, 2005, vol. 825 (2), pp. 98-110.
Guo T., et al., "Steroid Profiles Using Liquid Chromatography-Tandem Mass Spectrometry with Atmospheric Pressure Photoionization Source," Archives of Pathology & Laboratory Medicine, 2004, vol. 128 (4), pp. 469-475.
Hashizume T., et al., "Identification of Human UDP-Glucuronosyltransferases Catalyzing Hepatic 1a,25-Dihydroxyvitamin D3 Conjugation," Biochemical Pharmacology, 2008, vol. 75 (5), pp. 1240-1250.
Heudi O., et al., "Simultaneous Quantification of Vitamins A, D3 and E in Fortified Infant Formulae by Liquid Chromatography-Mass Spectrometry," Journal of Chromatography, 2004, vol. 1022 (1-2), pp. 115-123.
Higashi T., et al., "Application of 4-(4-Nitrophenyl)-1,2,4-triazoline-3,5-dione to Analysis of 25-Hydroxyvitamin D3 in Human Plasma by Liquid Chromatography/Electron Capture Atmospheric Pressure Chemical Ionization-Mass Spectrometry," Analytical Sciences, 2003, vol. 19 (6), pp. 941-943.
Higashi T., et al., "Characterization of New Conjugated Metabolites in Bile of Rats Administered 24, 25-Dihydroxyvitamin D3 and 25-Hydroxyvitamin D3," Steroids, 2000, vol. 65 (5), pp. 281-294.
Higashi T., et al., "Characterization of Urinary Metabolites of Vitamin D3 in Man under Physiological Conditions Using Liquid Chromatography-Tandem Mass Spectrometry," Journal of Pharmaceutical and Biomedical Analysis, 2002, vol. 29 (5), pp. 947-955.
Higashi T., et al., "Determination of 24, 25-Dihydroxyvitamin D3 in Human Plasma Using Liquid Chromatography-Mass Spectrometry after Derivatization with a Cookson-Type Reagent," Journal of Chromatography, 2001, vol. 15 (2), pp. 133-140.
Higashi T., et al., "Simultaneous Determination of 25-Hydroxyvitamin D2 and 25-Hydroxyvitamin D3 in Human Plasma by Liquid Chromatography-Tandem Mass Spectrometry Employing Derivatization with a Cookson-Type Reagent," Biological & Pharmaceutical Bulletin, 2001, vol. 24 (7), pp. 738-743.
Higashi T., et al., "Liquid Chromatography-Mass Spectrometric Method Combined With Derivatization for Determination of 1 Alpha-Hydroxyvitamin D (3) In Human Plasma," Journal of Chromatography B, 2002, vol. 772 (2), pp. 229-238.
Higashi T., et al., "Liquid Chromatography-Tandem Mass Spectrometric Method for the Determination of Salivary 25-Hydroxyvitamin D3: A Noninvasive Tool for the Assessment of Vitamin D Status," Analytical and Bioanalytical Chemistry, 2008, vol. 391 (1), pp. 229-238.
Higashi T., et al., "Usefulness of Derivatization in High-Performance Liquid Chromatography/Tandem Mass Spectrometry of Conjugated Vitamin D Metabolites," Analytical Sciences, 1999, vol. 15, pp. 619-623.
International Preliminary Report and Written Opinion on Patentability for Application No. PCT/US2010/059746, dated Jun. 12, 2012.
International Preliminary Report and Written Opinion on Patentability for Application No. PCT/US2010/059771, dated Jun. 12, 2012.
International Preliminary Report on Patentability for Application No. PCT/US2006/012539, dated Oct. 9, 2007.
International Preliminary Report on Patentability for Application No. PCT/US2008/084709, dated Jun. 1, 2010.
International Preliminary Report on Patentability for Application No. PCT/US2010/056886, dated Jun. 5, 2012.
International Preliminary Report on Patentability for Application No. PCT/US2010/057627, dated Jun. 5, 2012.
International Preliminary Report on Patentability for Application No. PCT/US2010/059765, dated Jun. 12, 2012.
International Search Report and Written Opinion for Application No. PCT/US2010/056461, dated Jan. 26, 2011.
International Search Report and Written Opinion for Application No. PCT/US2010/057627, dated Jan. 27, 2011.
International Search Report and Written Opinion for Application No. PCT/US2010/059746, dated Feb. 8, 2011.
International Search Report and Written Opinion for Application No. PCT/US2010/059765, dated Feb. 7, 2011.
International Search Report for Application No. PCT/US2006/012539, dated Jan. 4, 2007.
International Search Report for Application No. PCT/US2008/084709, dated Feb. 24, 2009.
International Search Report for Application No. PCT/US2010/056886, dated Jan. 14, 2011.
International Search Report for Application No. PCT/US2010/059771, dated Feb. 11, 2011.
Jemal M., et al., "High-Throughput Quantitative Bioanalysis by LC/MS/MS," Biomedical Chromatography, 2000, vol. 14 (6), pp. 422-429.
Jessome L.L., et al., "Ion Suppression: A Major Concern in Mass Spectrometry," Advanstar Communications Inc, 2006, vol. 24 (5), pp. 498-510.
Jones et al., "Vitamin Ds: Metabolites and Analogs. Chapter 2 in Modem Chromatographic Analysis of Vitamins", 3rd Edition, Leenheer et al., eds., New York: Marcel Dekker, Inc., 2002, 79 pages.
Jones G., et al., "Biological Activity of 1,25-Dihydroxyvitamin D2 in the Chick," Biochemistry, 1976, vol. 15 (3), pp. 713-716.
Jones G., et al., "Current Understanding of the Molecular Actions of Vitamin D," Third Edition, 2002, 79 pgs., Physiological Reviews, 1998, vol. 78 (4), pp. 1193-1231.
Kamao M., et al., "C-3 Epimerization of Vitamin D3 Metabolites and Further Metabolism of C-3 Epimers," The Journal of Biological Chemistry, 2004, vol. 279 (16), pp. 15897-15907.
Kamao M., et al., "Quantification of Fat-Soluble Vitamins in Human Breast Milk by Liquid Chromatography-tandem Mass Spectrometry," Journal of Chromatography B, 2007, vol. 859 (2), pp. 192-200.
Kissmeyer A.M., et al., "Sensitive Analysis of 1 alpha, 25-Dihydroxyvitamin D3 in Biological Fluids by Liquid Chromatography-Tandem Mass Spectrometry," Journal of Chromatography A, 2001, vol. 935 (1-2), pp. 93-103.
Kobayashi N., et al., "Production of a Group-Specific Antibody to 1alpha, 25-Dihydroxyvitamin D and Its Derivatives Having the 1alpha, 3beta-Dihydroxylated A-Ring Structure," Steroids, 1994, vol. 59 (7), pp. 404-411.
Kobayashi N., et al., "Tandem Immunoaffinity Chromatography for Plasma 1 Alpha, 25-Dihydroxyvitamin D3 Utilizing Two Antibodies Having Different Specificities: A Novel and Powerful Pretreatment Tool for 1 Alpha, 25-Dihydroxyvitamin D3 Radioreceptor Assays," The Journal of Steroid Biochemistry and Molecular Biology, 1995, vol. 54 (5-6), pp. 217-226.
LC-MS: Why use it, and what is it?, Metabolite Services at JIC [online], [retrieved on Sep. 6, 2014]. Retrieved from the Internet: URL: https://WMN.jic.ac.uk/services/metabolomics/topics/lcms/why.htm.
Letter from Norton V.G., Ph.D. Partner, Duane Morris LLP, Sep. 4, 2008.
Luque De Castro M.D., et al., "Determination of Vitamin D3 Metabolites: State-Of-The-Art and Trends," Journal of Pharmaceutical and Biomedical Analysis, 1999, vol. 20 (1-2), pp. 1-17.

(56) References Cited

OTHER PUBLICATIONS

Magalhaes, P. J., et al., "Detection and Quantification of Provitamin D2 and Vitamin D2 in Hop (*Humulus lupulus* L.) by Liquid Chromatography-Diode Array Detection-Electrospray Ionization Tandem Mass Spectrometry.," Journal of Agricultural and Food Chemistry, 2007, vol. 55 (20), pp. 7995-8002.
Maunsell Z., et al., "Routine Isotope-Dilution Liquid Chromatography-Tandem Mass Spectrometry Assay for Simultaneous Measurement of the 25-Hydroxy Metabolites of Vitamins D2 and D3," Clinical Chemist, 2005, vol. 51 (9), pp. 1683-1690.
Merchant M., et al., "Recent Advancements in Surface-Enhanced Laser Desorption/Ionization-Time of Flight-Mass Spectrometry," Electrophoresis, 2000, vol. 21 (6), pp. 1164-1167.
Miller W.L., et al., "Genetic Causes of Rickets," Current Opinions in Pediatrics, 1999, vol. 11 (4), pp. 333-339.
Mitamura K., et al., "Derivatization in Lc Ms," Yakugaku Zasshi, 1998, vol. 118 (6), pp. 206-215.
Murao N., et al., "Ferrocene-Based Diels-Alder Derivatization for the Determination of 1alpha-Hydroxyvitamin D3 in Rat Plasma by High-Performance Liquid Chromatography-Electrospray Tandem Mass Spectrometry," Analytical Biochemistry, 2005, vol. 346 (1), pp. 158-166.
Non-Final Office Action dated May 2, 2017 for U.S. Appl. No. 15/388,844, filed Dec. 22, 2016.
Non-Final Office Action dated Jul. 3, 2017 for U.S. Appl. No. 15/194,009, filed Jun. 27, 2016.
Non-Final Office Action dated May 3, 2016 for U.S. Appl. No. 14/639,834, filed Mar. 5, 2015.
Non-Final Office Action dated Aug. 4, 2011 for U.S. Appl. No. 13/115,916, filed May 25, 2011.
Non-Final Office Action dated Oct. 5, 2010 for U.S. Appl. No. 11/386,215, filed Mar. 21, 2006.
Non-Final Office Action dated Jul. 7, 2010 for U.S. Appl. No. 12/630,796, filed Dec. 3, 2009.
Non-Final Office Action dated Oct. 8, 2008 for U.S. Appl. No. 11/101,166, filed Apr. 6, 2005.
Non-Final Office Action dated Apr. 9, 2013 for U.S. Appl. No. 13/287,012, filed Nov. 1, 2011.
Non-Final Office Action dated Sep. 10, 2014 for U.S. Appl. No. 12/964,710, filed Dec. 9, 2010.
Non-Final Office Action dated Dec. 11, 2013 for U.S. Appl. No. 14/063,956, filed Oct. 25, 2013.
Non-Final Office Action dated Mar. 11, 2013 for U.S. Appl. No. 13/751,915, filed Jan. 28, 2013.
Non-Final Office Action dated Sep. 11, 2013 for U.S. Appl. No. 13/871,457, filed Apr. 26, 2013.
Non-Final Office Action dated Apr. 12, 2010 for U.S. Appl. No. 11/386,215, filed Mar. 21, 2006.
Non-Final Office Action dated Dec. 12, 2014 for U.S. Appl. No. 14/063,956, filed Oct. 25, 2011.
Non-Final Office Action dated Jan. 12, 2016 for U.S. Appl. No. 14/715,153, filed May 18, 2015.
Non-Final Office Action dated Feb. 13, 2013 for U.S. Appl. No. 12/964,717, filed Dec. 9, 2010.
Non-Final Office Action dated Mar. 13, 2012 for U.S. Appl. No. 13/327,650, filed Dec. 15, 2011.
Non-Final Office Action dated Oct. 15, 2012 for U.S. Appl. No. 12/964,710, filed Dec. 9, 2010.
Non-Final Office Action dated Dec. 18, 2017 for U.S. Appl. No. 14/639,834, filed Mar. 5, 2015.
Asperger A., et al., "Trace Determination of Priority Pesticides in Water by Means of High-Speed On-Line Solid-Phase Extraction-Liquid Chromatography-Tandem Mass Spectrometry Using Turbulent-Flow Chromatography Columns for Enrichment and a Short Monolithic Column for Fast Liquid Chromatographic Separation," Journal of Chromatography A, Jun. 2002, vol. 960 (1-2), pp. 109-119.
Casetta B., et al., "Development of a Method for the Quantification of 1alpha,25(OH)2-Vitamin D3 in Serum by Liquid Chromatography Tandem Mass Spectrometry Without Derivatization," European Journal of Mass Spectrometry, 2010, vol. 16 (1), pp. 81-89.

Chen Y., et al., "Organic Mass Spectrometry Principles and Applications," Science Press, 2001, 6 pages.
Danaceau J.P., et al., "Quantitative Confirmation of Testosterone and Epitestosterone in Human Urine by LC/Q-ToF Mass Spectrometry for Doping Control," Journal of Mass Spectrometry, Jul. 2008, vol. 43 (7), pp. 993-1000.
Grant R.P., et al., "Generic Serial and Parallel On-Line Direct-Injection Using Turbulent Flow Liquid Chromatography/tandem Mass Spectrometry," Rapid Communications in Mass Spectrometry, 2002, vol. 16 (18), pp. 1785-1792.
Iwase H., "Determination of Vitamin D-2 in Emulsified Nutritional Supplements by Solid-Phase Extraction and Column-Switching High-Performance Liquid Chromatography with UV Detection," Journal of Chromatography A, Jul. 2000, vol. 881 (1-2), pp. 189-196.
Masuda S., et al., "A Method for the Simultaneous Determination of Vitamins D2,D3 and Their Metabolites in Plasma and Its Application to Plasma Samples Obtained from Normal Subjects and Patients," Food Chemistry, 1992, vol. 45 (3), pp. 215-225.
Non-Final Office Action dated May 8, 2018 for U.S. Appl. No. 15/194,009, filed Jun. 27, 2016.
Non-Final Office Action dated Apr. 19, 2018 for U.S. Appl. No. 15/362,210, filed Nov. 28, 2016.
Ortiz-Boyer F., et al., "Quantitation of Circulating Hydroxyvitamin D3 in Human Plasma by a Continuous Cleanup/concentration Procedure Prior to HPLC-UV Detection," Clinica Chimica Acta, Jun. 1998, vol. 274 (2), pp. 139-149.
Patent Board Decision mailed Jun. 1, 2018 for U.S. Appl. No. 12/964,710, filed Dec. 9, 2010.
Shimizu M., et al., "Determination of 25-Hydroxyvitamin D3 in Human Plasma Using a Non-Radioactive Tetranorvitamin D Analogue as an Internal Standard," Journal of Chromatography B, Oct. 1995, vol. 672 (1), pp. 63-71.
Chang., Y., "New Technology of Tandem Mass Spectrometry and the Progress of Its Application in Drug Metabolism Research," Acta Pharmacologica Sinica, Jan. 2000, vol. 35 (1).
Examiner's Answer to Appeal Brief dated Sep. 17, 2018 for U.S. Appl. No. 14/267,014 filed May 1, 2014.
Hagar A.F., et al., "Reversed-Phase Liquid Chromatographic Determination of Vitamin D in Milk," Journal of AOAC International, 1994, vol. 77 (4), pp. 1047-1051.
Higashi T., "Trace Determination of Steroids Causing Age-Related Diseases Using LC/MS Combined with Detection-Driented Derivatization," Chemical & Pharmaceutical Bulletin, Nov. 2006, vol. 54 (11), pp. 1479-1485.
Non-Final Office Action dated Oct. 5, 2018 for U.S. Appl. No. 15/489,551 filed Apr. 17, 2017.
Non-Final Office Action dated Feb. 6, 2019 for U.S. Appl. No. 15/362,210 filed Nov. 28 2016.
Non-Final Office Action dated Oct. 15, 2018 for U.S. Appl. No. 14/639,834 filed Mar. 5, 2015.
Non-Final Office Action dated Jan. 31, 2019 for U.S. Appl. No. 15/194,009 filed Jun. 27, 2016.
Shimada K., et al., "Cookson-Type Reagents: Highly Sensitive Derivatization Reagents for Conjugated Dienes in High-Performance Liquid Chromatography," The Analyst, Dec. 1991, vol. 116 (12), pp. 1393-1397.
Shimada K., et al., "Retention Behavior of Vitamin D and Related Compounds During High-Performance Liquid chromatography," Journal of Liquid Chromatography, 1995, vol. 18 (14), pp. 2885-2893.
Wilson S.R., et al., "Analysis of Vitamin D and Its Metabolites: Derivatization and Detection by Electrospray Ionization Mass Spectrometry," Journal of the Chemical Society, Chemical Communications, 1993, pp. 664-665.
Written Opinion for Application No. PCT/US2010/056886, dated Jan. 14, 2011.
Yan C., et al., "New Techniques of Tandem Mass Spectrometry and Its Application in the Study of Drug Metabolism," Acta Pharmaceutica Sinica, 2000, vol. 35(1), pp. 73-78.

\* cited by examiner

METHODS FOR DETECTING VITAMIN D METABOLITES BY MASS SPECTROMETRY

CROSS REFERENCE TO RELATED PATENT APPLICATIONS

This application is a continuation of U.S. application Ser. No. 15/388,844, filed Dec. 22, 2016, now U.S. Pat. No. 9,880,180, which is a continuation of U.S. application Ser. No. 15/005,801, filed Jan. 25, 2016, now U.S. Pat. No. 9,529,004, which is a continuation of U.S. application Ser. No. 14/180,722, filed Feb. 14, 2014, now U.S. Pat. No. 9,244,084, which is a continuation of U.S. application Ser. No. 13/871,457, now U.S. Pat. No. 8,936,943, filed Apr. 26, 2013, which is a continuation of U.S. application Ser. No. 13/327,650, now U.S. Pat. No. 8,431,411, filed Dec. 15, 2011, which is a continuation of U.S. application Ser. No. 13/115,916, now U.S. Pat. No. 8,101,427, filed May 25, 2011, which is a continuation of U.S. application Ser. No. 11/386,215, now U.S. Pat. No. 7,972,867, filed Mar. 21, 2006, which is a continuation-in-part of U.S. application Ser. No. 11/101,166, now U.S. Pat. No. 7,745,226, filed Apr. 6, 2005, each of which is incorporated by reference in its entirety herein.

TECHNOLOGY FIELD

The invention relates to the detection of vitamin D metabolites. In a particular aspect, the invention relates to methods for detecting vitamin D metabolites by mass spectrometry.

BACKGROUND

Vitamin D is an essential nutrient with important physiological roles in the positive regulation of calcium ($Ca^{2+}$) homeostasis. Vitamin D can be made de novo in the skin by exposure to sunlight or it can be absorbed from the diet. There are two forms of vitamin D; vitamin $D_2$ (ergocalciferol) and vitamin $D_3$ (cholecalciferol). Vitamin $D_3$ is the form synthesized de novo by animals. It is also a common supplement added to milk products and certain food products produced in the United States. Both dietary and intrinsically synthesized vitamin $D_3$ must undergo metabolic activation to generate bioactive metabolites. In humans, the initial step of vitamin $D_3$ activation occurs primarily in the liver and involves hydroxylation to form the intermediate metabolite 25-hydroxyvitamin $D_3$ (25-hydroxycholecalciferol; calcifediol; $25OHD_3$). Calcifediol is the major form of vitamin $D_3$ in the circulation. Circulating $25OHD_3$ is then converted by the kidney to 1,25-dihydroxyvitamin $D_3$ (calcitriol; $1,25(OH)_2D_3$), which is generally believed to be the metabolite of vitamin $D_3$ with the highest biological activity.

Vitamin $D_2$ is derived from fungal and plant sources. Many over-the-counter dietary supplements contain ergocalciferol (vitamin $D_2$) rather than cholecalciferol (vitamin $D_3$). Drisdol, the only high-potency prescription form of vitamin D available in the United States, is formulated with ergocalciferol. Vitamin $D_2$ undergoes a similar pathway of metabolic activation in humans as vitamin $D_3$, forming the metabolites 25-hydroxyvitamin $D_2$ ($25OHD_2$) and 1,25-dihydroxyvitamin $D_3$ ($1,25(OH)_2D_2$). Vitamin $D_2$ and vitamin $D_3$ have long been assumed to be biologically equivalent in humans, however recent reports suggest that there may be differences in the bioactivity and bioavailability of these two forms of vitamin D (Armas et. al., (2004) J. Clin. Endocrinol. Metab. 89:5387-5391).

Measurement of vitamin D, the inactive vitamin D precursor, is rare in clinical settings and has little diagnostic value. Rather, serum levels of 25-hydroxyvitamin $D_3$ and 25-hydroxyvitamin $D_2$ (total 25-hydroxyvitamin D; "25OHD") are a useful index of vitamin D nutritional status and the efficacy of certain vitamin D analogs. Therefore, the measurement of 25OHD is commonly used in the diagnosis and management of disorders of calcium metabolism. In this respect, low levels of 25OHD are indicative of vitamin D deficiency associated with diseases such as hypocalcemia, hypophosphatemia, secondary hyperparathyroidism, elevated alkaline phosphatase, osteomalacia in adults and rickets in children. In patients suspected of vitamin D intoxication, elevated levels of 25OHD distinguishes this disorder from other disorders that cause hypercalcemia.

Measurement of $1,25(OH)_2D$ is also used in clinical settings, however, this metabolite has a more limited diagnostic usefulness than 25OHD. Factors that contribute to limitations of the diagnostic values of $1,25(OH)_2D$ as an index of vitamin D status include the precision of the endogenous regulation of renal production of the metabolite and its short half-life in circulation. However, certain disease states such as kidney failure can be diagnosed by reduced levels of circulating $1,25(OH)_2D$ and elevated levels of $1,25(OH)_2D$ may be indicative of excess parathyroid hormone or may be indicative of certain diseases such as sarcoidosis or certain types of lymphoma.

Detection of vitamin D metabolites has been accomplished by radioimmunoassay with antibodies co-specific for 25-hydroxyvitamin $D_3$ and 25-hydroxyvitamin $D_2$. Because the current immunologically-based assays do not separately resolve 25-hydroxyvitamin $D_3$ and 25-hydroxyvitamin $D_2$, the source of a deficiency in vitamin D nutrition cannot be determined without resorting to other tests. More recently, reports have been published that disclose methods for detecting specific vitamin D metabolites using mass spectrometry. For example Yeung B, et al., J Chromatogr. 1993, 645(1):115-23; Higashi T, et al., Steroids. 2000, 65(5):281-94; Higashi T, et al., Biol Pharm Bull. 2001, 24(7):738-43; and Higashi T, et al., J Pharm Biomed Anal. 2002, 29(5):947-55 disclose methods for detecting various vitamin D metabolites using liquid chromatography and mass spectrometry. These methods require that the metabolites be derivatized prior to detection by mass-spectrometry. Methods to detect underivatized $1,25(OH)_2D_3$ by liquid chromatography/mass-spectrometry are disclosed in Kissmeyer and Sonne, J Chromatogr A. 2001, 935(1-2):93-103.

SUMMARY

The present invention provides methods for detecting the presence or amount of a vitamin D metabolite in a sample by mass spectrometry, including tandem mass spectrometry. Preferably, the methods of the invention do not include derivatizing the vitamin D metabolites prior to the mass spectrometry analysis.

In one aspect, the invention provides a method for determining the presence or amount of a vitamin D metabolite in a sample. The method may include: (a) ionizing the vitamin D metabolite, if present in the sample; and (b) detecting the presence or amount of the ion by mass spectrometry and relating presence or amount of the detected ion to the presence or amount of the vitamin D metabolite in the sample. In some preferred embodiments, the ionization step (a) may include (i) ionizing the vitamin D metabolite, if present in the sample, to produce an ion of the vitamin D metabolite; (ii) isolating the ion of step (i) by mass spectrometry to provide a precursor ion; and (iii) effecting a collision between the precursor ion and an inert collision gas to produce at least one fragment ion detectable in a mass spectrometer. Preferably, at least one of the fragment ions is specific for the vitamin D metabolite of interest. In certain embodiments of the invention, the fragment ions to be detected include at least one fragment ion other than that which results solely by a dehydration or deamination of the precursor ion. In some particularly preferred embodiments, the precursor ion is a protonated and dehydrated ion of the vitamin D metabolite. In certain embodiments the vitamin D metabolite is one or more vitamin D metabolites selected from the group consisting of 25-hydroxyvitamin $D_3$; 25-hydroxyvitamin $D_2$; 1,25-dihydroxyvitamin $D_2$; and 1,25-dihydroxyvitamin $D_3$.

In a related aspect, the invention provides a method for determining the presence or amount of a vitamin D metabolite in a sample by tandem mass spectrometry. The method may involve (a) generating a protonated and dehydrated precursor ion of the vitamin D metabolite if present in the sample; (b) generating one or more fragment ions of the precursor ion; and (c) detecting the presence or amount of one or more of the ions generated in step (a) or (b) or both and relating the detected ions to the presence or amount of the vitamin D metabolite in the sample. In certain embodiments, the method is used to detect the presence or amount of two or more vitamin D metabolites in a single assay. Preferably, the method does not involve derivatizing the samples or the vitamin D metabolites prior to analysis by mass spectrometry. In certain embodiments the vitamin D metabolite is one or more vitamin D metabolites selected from the group consisting of 25-hydroxyvitamin $D_3$; 25-hydroxyvitamin $D_2$; 1,25-dihydroxyvitamin $D_2$; and 1,25-dihydroxyvitamin $D_3$.

In another aspect the invention provides a method for determining the presence or amount of two or more vitamin D metabolites in a sample in a single assay. The method includes ionizing the vitamin D metabolites, if present in the sample, to generate ions specific for each of the vitamin D metabolites of interest, detecting the presence or amount of the ions by mass spectrometry, and relating the presence or amount of the ions to the presence or amount of the vitamin D metabolites in the sample. In certain embodiments the mass spectrometry analysis of the method is tandem mass spectrometry.

As used herein, the term "vitamin D metabolite" refers to any chemical species that may be found in the circulation of an animal which is formed by a biosynthetic or metabolic pathway for vitamin D or a synthetic vitamin D analog. Vitamin D metabolites include forms of vitamin D that are generated by a biological organism, such as an animal, or that are generated by biotransformation of a naturally occurring form of vitamin D or a synthetic vitamin D analog. In certain preferred embodiments, a vitamin D metabolite is formed by the biotransformation of vitamin $D_2$ or vitamin $D_3$. In particularly preferred embodiments, the vitamin D metabolite is one or more compounds selected from the group consisting of 25-hydroxyvitamin $D_3$, 25-hydroxyvitamin $D_2$, 1,25-dihydroxyvitamin $D_3$ and 1,25-dihydroxyvitamin $D_2$.

As used herein, the term "purification" refers to a procedure that enriches the amount of one or more analytes of interest relative to one or more other components of the sample. Purification, as used herein does not require the isolation of an analyte from all others. In preferred embodiments, a purification step or procedure can be used to remove one or more interfering substances, e.g., one or more substances that would interfere with the operation of the instruments used in the methods or substances that may interfere with the detection of an analyte ion by mass spectrometry.

As used herein, "biological sample" refers to any sample from a biological source. As used herein, "body fluid" means any fluid that can be isolated from the body of an individual. For example, "body fluid" may include blood, plasma, serum, bile, saliva, urine, tears, perspiration, and the like.

As used herein, "derivatizing" means reacting two molecules to form a new molecule. Derivatizing agents may include isothiocyanate groups, dinitro-fluorophenyl groups, nitrophenoxycarbonyl groups, and/or phthalaldehyde groups.

As used herein, "chromatography" refers to a process in which a chemical mixture carried by a liquid or gas is separated into components as a result of differential distribution of the chemical entities as they flow around or over a stationary liquid or solid phase.

As used herein, "liquid chromatography" (LC) means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). "Liquid chromatography" includes reverse phase liquid chromatography (RPLC), high performance liquid chromatography (HPLC) and high turbulence liquid chromatography (HTLC).

As used herein, the term "HPLC" or "high performance liquid chromatography" refers to liquid chromatography in which the degree of separation is increased by forcing the mobile phase under pressure through a stationary phase, typically a densely packed column.

As used herein, the term "gas chromatography" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase As used herein, "mass spectrometry" (MS) refers to an analytical technique to identify compounds by their mass. MS technology generally includes (1) ionizing the compounds to form charged compounds; and (2) detecting the molecular weight of the charged compound and calculating a mass-to-charge ratio (m/z). The compound may be ionized and detected by any suitable means. A "mass spectrometer" generally includes an ionizer and an ion detector. See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 2:264-76 (1999); and Merchant and Weinberger, *Electrophoresis* 21:1164-67 (2000).

The term "electron ionization" as used herein refers to methods in which an analyte of interest in a gaseous or vapor phase interacts with a flow of electrons. Impact of the electrons with the analyte produces analyte ions, which may then be subjected to a mass spectrometry technique.

The term "chemical ionization" as used herein refers to methods in which a reagent gas (e.g. ammonia) is subjected to electron impact, and analyte ions are formed by the interaction of reagent gas ions and analyte molecules.

The term "fast atom bombardment" as used herein refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine.

The term "field desorption" as used herein refers to methods in which a non-volatile test sample is placed on an ionization surface, and an intense electric field is used to generate analyte ions.

The term "ionization" as used herein refers to the process of generating an analyte ion having a net electrical charge equal to one or more electron units. Negative ions are those having a net negative charge of one or more electron units, while positive ions are those having a net positive charge of one or more electron units.

The term "operating in negative ion mode" refers to those mass spectrometry methods where negative ions are detected. Similarly, "operating in positive ion mode" refers to those mass spectrometry methods where positive ions are detected.

The term "desorption" as used herein refers to the removal of an analyte from a surface and/or the entry of an analyte into a gaseous phase.

The term "about" as used herein in reference to quantitative measurements, refers to the indicated value plus or minus 10%.

DETAILED DESCRIPTION

Figure 1:
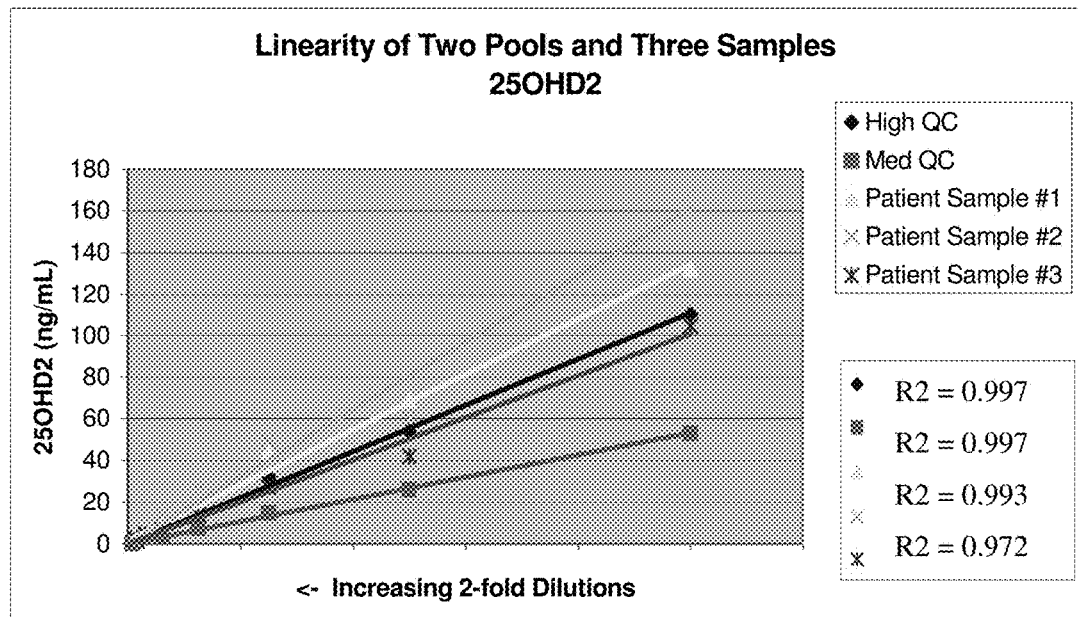
FIG. 1 shows the linearity of the quantification of 25OHD$_2$ in serially diluted stock samples using an LC-MS/MS assay. Details are described in Example 4.

Disclosed are methods for detecting the presence or amount of one or more vitamin D metabolites in a sample. In certain aspects the method involves ionizing the vitamin D metabolite(s), detecting the ion(s) by mass spectrometry, and relating the presence or amount of the ion(s) to the presence or amount of the vitamin D metabolite(s) in the sample. The method may include (a) purifying a vitamin D metabolite, if present in the sample, (b) ionizing the purified vitamin D metabolite and (c) detecting the presence or amount of the ion, wherein the presence or amount of the ion is related to the presence or amount of the vitamin D metabolite in the sample. In preferred embodiments, the ionizing step (b) may include (i) ionizing a vitamin D metabolite, if present in the sample, to produce an ion; (ii) isolating the vitamin D metabolite ion by mass spectrometry to provide a precursor ion; and (iii) effecting a collision between the isolated precursor ion and an inert collision gas to produce at least one fragment ion detectable in a mass spectrometer. In certain preferred embodiments the precursor ion is a protonated and dehydrated ion of the vitamin D metabolite.

In a related aspect, the invention provides a method for determining the presence or amount of a vitamin D metabolite in a test sample by tandem mass spectrometry. The method may involve (a) generating a protonated and dehydrated precursor ion of the vitamin D metabolite; (b) generating one or more fragment ions of the precursor ion; and (c) detecting the presence or amount of one or more of the ions generated in step (a) or (b) or both and relating the detected ions to the presence or amount of said vitamin D metabolite in the sample.

In certain preferred embodiments of the invention, at least one fragment ion is detected, wherein the presence or amount of the precursor and/or at least one fragment ion is related to the presence or amount of the vitamin D metabolite in the sample. Preferably at least one fragment ion is specific for the vitamin D metabolite of interest. In some embodiments, the methods of the invention can be used to detect and quantify two or more vitamin D metabolites in a single assay. In certain embodiments, the vitamin D metabolite is one or more vitamin D metabolites selected from the group consisting of 25-hydroxyvitamin D$_3$; 25-hydroxyvitamin D$_2$; 1,25-dihydroxyvitamin D$_2$; and 1,25-dihydroxyvitamin D$_3$.

Suitable samples include any sample that might contain the analyte of interest and/or one or more metabolites or precursors thereof. For example, samples obtained during the manufacture of an analyte can be analyzed to determine the composition and yield of the manufacturing process. In certain embodiments, a sample is a biological sample; that is, a sample obtained from any biological source, such as an animal, a cell culture, an organ culture, etc. Particularly preferred are samples obtained from a human, such as a blood, plasma, serum, hair, muscle, urine, saliva, tear, cerebrospinal fluid, or other tissue sample. Such samples may be obtained, for example, from a patient seeking diagnosis, prognosis, or treatment of a disease or condition. The vitamin D metabolites may be derivatized prior to mass spectrometry, however, in certain preferred embodiments, sample preparation excludes the use of derivatization.

Samples may be processed or purified to obtain preparations that are suitable for analysis by mass spectrometry. Such purification will usually include chromatography, such as liquid chromatography, and may also often involve an additional purification procedure that is performed prior to chromatography. Various procedures may be used for this purpose depending on the type of sample or the type of chromatography. Examples include filtration, extraction, precipitation, centrifugation, dilution, combinations thereof and the like. Protein precipitation is one preferred method of preparing a liquid biological sample, such as serum or plasma, for chromatography. Such protein purification methods are well known in the art, for example, Polson et al., *Journal of Chromatography B* 785:263-275 (2003), describes protein precipitation methods suitable for use in the methods of the invention. Protein precipitation may be used to remove most of the protein from the sample leaving vitamin D metabolites soluble in the supernatant. The samples can be centrifuged to separate the liquid supernatant from the precipitated proteins. The resultant supernatant can then be applied to liquid chromatography and subsequent mass spectrometry analysis. In one embodiment of the invention, the protein precipitation involves adding one volume of the liquid sample (e.g. plasma) to about four volumes of methanol. In certain embodiments, the use of protein precipitation obviates the need for high turbulence liquid chromatography ("HTLC") or on-line extraction prior to HPLC and mass spectrometry. Accordingly in such embodiments, the method involves (1) performing a protein precipitation of the sample of interest; and (2) loading the supernatant directly onto the HPLC-mass spectrometer without using on-line extraction or high turbulence liquid chromatography ("HTLC").

The purification step may include chromatography, preferably liquid chromatography, more preferably high performance liquid chromatography (HPLC). In some preferred embodiments the chromatography is not gas chromatography. Preferably, the methods of the invention are performed without subjecting the samples, or the vitamin D metabolites of interest, to gas chromatography prior to mass spectrometric analysis.

Various methods have been described involving the use of HPLC for sample clean-up prior to mass spectrometry analysis. See, e.g., Taylor et al., *Therapeutic Drug Monitoring* 22:608-12 (2000) (manual precipitation of blood samples, followed by manual C18 solid phase extraction, injection into an HPLC for chromatography on a C18 analytical column, and MS/MS analysis); and Salm et al., *Clin. Therapeutics* 22 Supl. B:B71-B85 (2000) (manual precipitation of blood samples, followed by manual C18 solid phase extraction, injection into an HPLC for chromatography on a C18 analytical column, and MS/MS analysis). One of skill in the art can select HPLC instruments and columns that are suitable for use in the invention. The chromatographic column typically includes a medium (i.e., a packing material) to facilitate separation of chemical moieties (i.e., fractionation). The medium may include minute particles. The particles include a bonded surface that interacts with the various chemical moieties to facilitate separation of the chemical moieties such as vitamin D metabolites. One suitable bonded surface is a hydrophobic bonded surface such as an alkyl bonded surface. Alkyl bonded surfaces may include C-4, C-8, or C-18 bonded alkyl groups, preferably C-18 bonded groups. The chromatographic column includes an inlet port for receiving a sample and an outlet port for discharging an effluent that includes the fractionated sample. In the method, the sample (or pre-purified sample) is applied to the column at the inlet port, eluted with a solvent or solvent mixture, and discharged at the outlet port. Different solvent modes may be selected for eluting the analytes of interest. For example, liquid chromatography may be performed using a gradient mode, an isocratic mode, or a polytyptic (i.e. mixed) mode. In preferred embodiments, HPLC is performed on a multiplexed analytical HPLC system with a C18 solid phase using isocratic separation with 100% methanol as the mobile phase.

Recently, high turbulence liquid chromatography ("HTLC"), also called high throughput liquid chromatography, has been applied for sample preparation prior to analysis by mass spectrometry. See, e.g., Zimmer et al., *J. Chromatogr. A* 854:23-35 (1999); see also, U.S. Pat. Nos. 5,968,367; 5,919,368; 5,795,469; and 5,772,874. Traditional HPLC analysis relies on column packings in which laminar flow of the sample through the column is the basis for separation of the analyte of interest from the sample. The skilled artisan will understand that separation in such columns is a diffusional process. In contrast, it is believed that turbulent flow, such as that provided by HTLC columns and methods, may enhance the rate of mass transfer, improving the separation characteristics provided. In some embodiments, high turbulence liquid chromatography (HTLC), alone or in combination with one or more purification methods, may be used to purify the vitamin D metabolite of interest prior to mass spectrometry. In such embodiments samples may be extracted using an HTLC extraction cartridge which captures the analyte, then eluted and chromatographed on a second HTLC column or onto an analytical HPLC column prior to ionization. Because the steps involved in these chromatography procedures can be linked in an automated fashion, the requirement for operator involvement during the purification of the analyte can be minimized. In certain embodiments of the method, samples are subjected to protein precipitation as described above prior to loading on the HTLC column; in alternative embodiments, the samples may be loaded directly onto the HTLC without being subjected to protein precipitation.

Recently, research has shown that epimerization of the hydroxyl group of the A-ring of vitamin $D_3$ metabolites is an important aspect of vitamin $D_3$ metabolism and bioactivation, and that depending on the cell types involved, 3-C epimers of vitamin $D_3$ metabolites (e.g., 3-epi-25(OH)$D_3$; 3-epi-24,25(OH)$_2D_3$; and 3-epi-1,25(OH)$_2D_3$) are often major metabolic products. See Kamao et al., *J. Biol. Chem.*, 279:15897-15907 (2004). Kamao et al., further provides methods of separating various vitamin D metabolites, including 3-C epimers, using Chiral HPLC. Accordingly, the invention also provides methods of detecting the presence, absence and/or amount of a specific epimer of one or more vitamin D metabolites, preferably vitamin $D_3$ metabolites, in a sample by (1) separating one or more specific vitamin D metabolites by chiral chromatography, preferably chiral HPLC; and (2) detecting the presence and/or amount of one or more vitamin D metabolites using mass spectrometry methods as described herein. The chiral chromatography procedures described in Kamao et al., are suitable for the methods of the invention, however, one of ordinary skill in the art understands that there are numerous other chiral chromatography methods that would also be suitable. In preferred embodiments the method includes, separating 25(OH)$D_3$ from 3-epi-25(OH)$D_3$, if present in a sample, using chiral chromatography; and detecting the presence and/or amount of the 25(OH)$D_3$ and the 3-epi-25(OH)$D_3$ in the sample using mass spectrometry. In related embodiments, the method includes separating 1α,25(OH)$_2D_3$ from 3-epi-1α,25(OH)$_2D_3$, if present in a sample, using chiral chromatography; and detecting the presence and/or amount of the 1α,25(OH)$_2D_3$ and the 3-epi-1α,25(OH)$_2D_3$ in the sample using mass spectrometry. In certain embodiments of the invention, chiral chromatography is used in conjunction with the HTLC methods described above.

Mass spectrometry is performed using a mass spectrometer which includes an ion source for ionizing the fractionated sample and creating charged molecules for further analysis. For example ionization of the sample may be performed by electrospray ionization (ESI), atmospheric pressure chemical ionization (APCI), photoinonization, electron ionization, fast atom bombardment (FAB)/liquid secondary ionization (LSIMS), matrix assisted laser desorption ionization (MALDI), field ionization, field desorption, thermospray/plasmaspray ionization, and particle beam ionization. The skilled artisan will understand that the choice of ionization method can be determined based on the analyte to be measured, type of sample, the type of detector, the choice of positive versus negative mode, etc.

After the sample has been ionized, the positively charged or negatively charged ions thereby created may be analyzed to determine a mass-to-charge ratio (i.e., m/z). Suitable analyzers for determining mass-to-charge ratios include quadropole analyzers, ion traps analyzers, and time-of-flight analyzers. The ions may be detected using several detection modes. For example, selected ions may be detected (i.e., using a selective ion monitoring mode (SIM)), or alternatively, ions may be detected using a scanning mode, e.g., multiple reaction monitoring (MRM) or selected reaction monitoring (SRM). Preferably, the mass-to-charge ratio is determined using a quadropole analyzer. For example, in a "quadrupole" or "quadrupole ion trap" instrument, ions in an oscillating radio frequency field experience a force proportional to the DC potential applied between electrodes, the amplitude of the RF signal, and m/z. The voltage and amplitude can be selected so that only ions having a particular m/z travel the length of the quadrupole, while all other ions are deflected. Thus, quadrupole instruments can act as both a "mass filter" and as a "mass detector" for the ions injected into the instrument.

One can often enhance the resolution of the MS technique by employing "tandem mass spectrometry," or "MS/MS." In this technique, a precursor ion (also called a parent ion) generated from a molecule of interest can be filtered in an MS instrument, and the precursor ion is subsequently fragmented to yield one or more fragment ions (also called daughter ions or product ions) that are then analyzed in a second MS procedure. By careful selection of precursor ions, only ions produced by certain analytes are passed to the fragmentation chamber, where collision with atoms of an inert gas to produce the daughter ions. Because both the precursor and fragment ions are produced in a reproducible fashion under a given set of ionization/fragmentation conditions, the MS/MS technique can provide an extremely powerful analytical tool. For example, the combination of filtration/fragmentation can be used to eliminate interfering substances, and can be particularly useful in complex samples, such as biological samples.

Additionally, recent advances in technology, such as matrix-assisted laser desorption ionization coupled with time-of-flight analyzers ("MALDI-TOF") permit the analysis of analytes at femtomole levels in very short ion pulses. Mass spectrometers that combine time-of-flight analyzers with tandem MS are also well known to the artisan. Additionally, multiple mass spectrometry steps can be combined in methods known as "MS/MS$^n$." Various other combinations may be employed, such as MS/MS/TOF, MALDI/MS/MS/TOF, or SELDI/MS/MS/TOF mass spectrometry.

The mass spectrometer typically provides the user with an ion scan; that is, the relative abundance of each ion with a particular m/z over a given range (e.g., 100 to 1000 amu). The results of an analyte assay, that is, a mass spectrum, can be related to the amount of the analyte in the original sample by numerous methods known in the art. For example, given that sampling and analysis parameters are carefully controlled, the relative abundance of a given ion can be compared to a table that converts that relative abundance to an absolute amount of the original molecule. Alternatively, molecular standards can be run with the samples, and a standard curve constructed based on ions generated from those standards. Using such a standard curve, the relative abundance of a given ion can be converted into an absolute amount of the original molecule. In certain preferred embodiments, an internal standard is used to generate a standard curve for calculating the quantity of the vitamin D metabolite. Methods of generating and using such standard curves are well known in the art and one of ordinary skill is capable of selecting an appropriate internal standard. For example, an isotope of a vitamin D metabolite may be used as an internal standard, in preferred embodiments the vitamin D metabolite is a deuterated vitamin D metabolite, for example $^6$D-25OHD$_3$. Numerous other methods for relating the presence or amount of an ion to the presence or amount of the original molecule will be well known to those of ordinary skill in the art.

One or more steps of the methods of the invention can be performed using automated machines. In certain embodiments, one or more purification steps are performed on line, and more preferably all of the purification and mass spectrometry steps may be performed in an on-line fashion.

In particularly preferred embodiments vitamin D metabolites are detected and/or quantified using LC-MS/MS as follows. The samples are subjected to liquid chromatography, preferably HPLC, the flow of liquid solvent from the chromatographic column enters the heated nebulizer interface of a LC-MS/MS analyzer and the solvent/analyte mixture is converted to vapor in the heated tubing of the interface. The analytes (i.e. vitamin D metabolites), contained in the nebulized solvent, are ionized by the corona discharge needle of the interface, which applies a large voltage to the nebulized solvent/analyte mixture. The ions, i.e. precursor ions, pass through the orifice of the instrument and enter the first quadrupole. Quadrupoles 1 and 3 (Q1 and Q3) are mass filters, allowing selection of ions (i.e., "precursor" and "fragment" ions) based on their mass to charge ratio (m/z). Quadrupole 2 (Q2) is the collision cell, where ions are fragmented. The first quadrupole of the mass spectrometer (Q1) selects for molecules with the mass to charge ratios of the specific vitamin D metabolites to be analyzed. Precursor ions with the correct m/z ratios of the precursor ions of specific vitamin D metabolites are allowed to pass into the collision chamber (Q2), while unwanted ions with any other m/z collide with the sides of the quadrupole and are eliminated. Precursor ions entering Q2 collide with neutral Argon gas molecules and fragment. This process is called Collision Activated Dissociation (CAD). The fragment ions generated are passed into quadrupole 3 (Q3), where the fragment ions of the desired vitamin D metabolites are selected while other ions are eliminated.

The methods of the invention may involve MS/MS performed in either positive or negative ion mode. Using standard methods well known in the art, one of ordinary skill is capable of identifying one or more fragment ions of a particular precursor ion of a vitamin D metabolite that can be used for selection in quadrupole 3 (Q3). Preferably, at least one fragment ion of the method is specific for the particular vitamin D metabolite of which detection is desired. A specific fragment ion for a particular vitamin D metabolite is one that will not be formed in significant amounts by other molecules with similar molecular structures. In contrast a non-specific fragment ion is one that is formed by related molecules other than the desired analyte. Therefore, detection of non-specific fragment ions alone is not reliable for distinguishing the desired vitamin D metabolite from other molecules that form the same or similar fragment ions. Specific fragment ions of a particular vitamin D metabolite can be identified by testing various molecular standards (e.g. vitamin D metabolites other than the metabolite to be detected) to determine whether fragment ions formed by the vitamin D metabolite of interest are also formed by other molecules with similar structures or features. In certain particularly preferred embodiments, a specific fragment ion is identified by testing at least one molecular standard that forms a precursor ion with the same m/z as the vitamin D metabolite to be detected.

If the precursor ion of a vitamin D metabolite of interest includes an alcohol or amine group, fragment ions are commonly formed that represent a dehydration or deamination of the precursor ion, respectfully. In the case of precursor ions that include an alcohol group, such fragment ions formed by dehydration are caused by a loss of one or more water molecules from the precursor ion (i.e., where the difference in m/z between the precursor ion and fragment ion is about 18 for the loss of one water molecule, or about 36 for the loss of two water molecules, etc.). In the case of precursor ions that include an amine group, such fragment ions formed by deamination are caused by a loss of one or more ammonia molecules (i.e. where the difference in m/z between the precursor ion and fragment ion is about 17 for the loss of one ammonia molecule, or about 34 for the loss of two ammonia molecules, etc.). Likewise, precursor ions that include one or more alcohol and amine groups commonly form fragment ions that represent the loss of one or more water molecules and/or one or more ammonia molecules (e.g., where the difference in m/z between the precursor ion and fragment ion is about 35 for the loss of one water molecule and the loss of one ammonia molecule). Generally, the fragment ions that represent dehydrations or deaminations of the precursor ion are not specific fragment ions for a particular analyte. For example, MS/MS performed to detect $25OHD_2$ by selecting for a precursor ion at 413 m/z (i.e. the protonated and hydrated ion) and detecting a fragment ion of 395 m/z (representing a dehydration of the 413 m/z precursor ion) would not be able to distinguish $25OHD_2$ from $1\alpha(OH)D_2$ which would form the same precursor and fragment ions. Therefore a 395 m/z fragment ion is not a specific fragment ion for $25OHD_2$ or $1\alpha(OH)D_2$. Accordingly, in preferred embodiments of the invention, MS/MS is performed such that at least one fragment ion of a vitamin D metabolite is detected that does not represent only a loss of one or more water molecules and/or a loss of one or more ammonia molecules from the precursor ion.

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC methods. The areas under the peaks corresponding to particular ions, or the amplitude of such peaks, are measured and the area or amplitude is correlated to the amount of the analyte (vitamin D metabolite) of interest. In certain embodiments, the area under the curves, or amplitude of the peaks, for fragment ion(s) and/or precursor ions are measured to determine the amount of a vitamin D metabolite. As described above, the relative abundance of a given ion can be converted into an absolute amount of the original analyte, i.e., vitamin D metabolite, using calibration standard curves based on peaks of one or more ions of an internal molecular standard, such as $^6D\text{-}25OHD_3$.

In certain aspects of the invention, the quantity of various ions is determined by measuring the area under the curve or the amplitude of the peak and a ratio of the quantities of the ions is calculated and monitored (i.e. "daughter ion ratio monitoring"). In certain embodiments of the method, the ratio(s) of the quantity of a precursor ion and the quantity of one or more fragment ions of a vitamin D metabolite can be calculated and compared to the ratio(s) of a molecular standard of the vitamin D metabolite similarly measured. In embodiments where more than one fragment ion of a vitamin D metabolite is monitored, the ratio(s) for different fragment ions may be determined instead of, or in addition to, the ratio of the fragment ion(s) compared to the precursor ion. In embodiments where such ratios are monitored, if there is a substantial difference in an ion ratio in the sample as compared to the molecular standard, it is likely that a molecule in the sample is interfering with the results. To the contrary, if the ion ratios in the sample and the molecular standard are similar, then there is increased confidence that there is no interference. Accordingly, monitoring such ratios in the samples and comparing the ratios to those of authentic molecular standards may be used to increase the accuracy of the method.

In certain aspects of the invention, MS/MS is performed in positive ion mode with the first quadruple (Q1) tuned to select for precursor ions with a mass charge ratio corresponding to protonated and dehydrated ions of vitamin D metabolites. The mass/charge ratio (m/z) for the protonated and dehydrated precursor vitamin D metabolite ions is about 383.16 m/z for 25-hydroxyvitamin $D_3$ and about 395.30 m/z for 25-hydroxyvitamin $D_2$. In embodiments where the samples are spiked with hexadeuterated $25OHD_3$ ($^6D\text{-}25OHD_3$) for use as an internal standard, the mass/charge ratio (m/z) of the protonated and dehydrated $^6D\text{-}25OHD_3$ precursor ion is about 389.20. In certain preferred embodiments of the invention, the mass/charge ratio (m/z) for the 25-hydroxyvitamin $D_3$ precursor ion is about 383.16 and the m/z for at least one 25-hydroxyvitamin $D_3$ fragment ion is about 211.35. In related embodiments, the m/z for the 25-hydroxyvitamin $D_2$ precursor ion is about 395.30 and the 25-hydroxyvitamin $D_2$ fragment ion(s) include one or more ions selected from the group consisting of ions with mass/charge ratios (m/z) of about 179.10, about 209.20 and about 251.30. In embodiments where the samples are spiked with $^6D\text{-}25OHD_3$ for use as an internal standard the mass/charge ratio (m/z) for the protonated and dehydrated $^6D\text{-}25OHD_3$ precursor ion is about 389.20 and the fragment ion(s) may include a fragment ion with a m/z of about 211.30.

In other aspects, MS/MS is performed in positive ion mode with the first quadruple (Q1) tuned to select for precursor ions with a mass charge ratio corresponding to protonated and hydrated ions of vitamin D metabolites. The mass/charge ratio (m/z) for the protonated and hydrated precursor vitamin D metabolite ions are about 401 m/z for 25-hydroxyvitamin $D_3$ and about 413 m/z for 25-hydroxyvitamin $D_2$. In certain preferred embodiments of the invention, the mass/charge ratio (m/z) for the 25-hydroxyvitamin $D_3$ precursor ion is about 401 and the 25-hydroxyvitamin $D_3$ fragment ion(s) include one or more ions selected from the group consisting of ions with mass/charge ratios (m/z) of about 365 and about 383 m/z; more preferably the fragment ions include an ion with a m/z of about 365. In related embodiments, the m/z for the protonated and hydrated 25-hydroxyvitamin $D_2$ precursor ion is about 413 m/z, and the 25-hydroxyvitamin $D_2$ fragment ion(s) include one or more ions with mass/charge ratios (m/z) of about 377 and about 395; more preferably the fragment ions include an ion with a mass charge ratio of about 377.

In particularly preferred embodiments of the invention, the presence or absence or amount of two or more vitamin D metabolites in a sample are detected in a single assay using the above described MS/MS methods.

Mass spectrometry instruments can vary slightly in determining the mass of a given analyte. Thus, the term "about" in the context of mass of an ion or the m/z of an ion refers to +/−0.5 atomic mass unit.

The following examples serve to illustrate the invention. These examples are in no way intended to limit the scope of the invention.

EXAMPLES

Example 1: Determination of 25-hydroxyvitamin $D_3$ and 25-hydroxyvitamin $D_2$ by LC-MS/MS Using a Perkin-Elmer MultiProbe II (S/N 432400) robotic liquid handler, human serum samples were first extracted using a protein precipitation method by adding 42.5 µl of serum to 170 µl of methanol (1:4 ratio of serum:methanol) in a 96-well plate format. For validation-related experiments, the methanol was spiked with hexadeuterated $25OHD_3$ ($^6D$-$25OHD_3$) as an internal standard. The 96 well plates were centrifuged to remove precipitated protein, leaving the vitamin D metabolites in the supernatant. The supernatants were then transferred to an HPLC autosampler for loading to the LC-MS/MS analyzer.

LC-MS/MS was performed using a Thermo Finnigan LC-MS/MS analyzer (Thermo Finnigan Quantum TSQ (S/N: TQU00655)) with an atmospheric pressure chemical ionization (APCI) source as the detector. An autosampler was used to inject 50 µL of extracted sample supernatant onto an HPLC column. Liquid chromatography was performed with a Cohesive Technologies Aria TX-4 (S/N: SJCTX409) LC system with Waters Symmetry C18 5 µm 4.6×50 mm columns using 100% methanol as the mobile phase. After the analytes eluted and the detector window completed acquisition, the system was washed with 85% Mobile phase A and then re-equilibrated with Mobile phase B for a run time of 5 minutes. Mobile phase A was 0.1% formic acid in HPLC-grade water and mobile phase B was 100% methanol.

The flow of liquid solvent exiting the HPLC column entered the heated nebulizer interface of the Thermo Finnigan LC-MS/MS analyzer. The solvent/analyte mixture was first converted to vapor in the heated tubing of the interface. The analytes, contained in the nebulized solvent, were ionized (a positive charge added) by the corona discharge needle of the interface, which applies a large voltage to the nebulized solvent/analyte mixture. The ions pass through the orifice of the instrument and enter the first quadrupole. Quadrupoles 1 and 3 (Q1 and Q3) are mass filters, allowing selection of ions based on their mass to charge ratio (m/z). Quadrupole 2 (Q2) is the collision cell, where ions are fragmented.

The first quadrupole of the mass spectrometer (Q1) selected for molecules with the mass to charge ratios of (protonated and dehydrated) $25OHD_2$, $25OHD_3$ and $^6D$-$25OHD_3$. Ions with these m/z ratios (see table below) were allowed to pass into the collision chamber (Q2), while unwanted ions with any other m/z collide with the sides of the quadrupole and are eliminated. Ions entering Q2 collide with neutral Argon gas molecules and fragment. The fragment ions generated are passed into quadrupole 3 (Q3), where the fragment ions of $25OHD_2$, $25OHD_3$ and $^6D$-$25OHD_3$ were selected (see table below) and other ions are eliminated. The following mass transitions were used for detection and quantitation during validation:

TABLE 1

Mass transitions for selected vitamin D metabolites

| Compound | Precursor Ion (m/z) | Fragment Ions (m/z) |
|---|---|---|
| $25OHD_2$ | 395.30 | 179.10, 251.30, 209.20 |
| $25OHD_3$ | 383.16 | 211.35 |
| $^6D$-$25OHD_3$ | 389.20 | 211.30 |

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC methods.

Area ratios of the analyte and internal standard (Hexadeuterated 25-Hydroxyvitamin D3, $^6D$-$25OHD_3$) peaks were used to construct calibration curves, which were then used to calculate analyte concentrations. Using the calibration curves, the concentrations of $25OHD_2$ and 25OHD3 were quantitated in the patient samples.

Example 2: Intra-Assay and Inter-Assay Precision

Stock solutions of $25OHD_2$ and $25OHD_3$ were added to pooled serum to produce a Low Pool (20-25 ng/mL of each metabolite), a Medium Pool (45-55 ng/mL of each metabolite) and a High Pool (100-110 ng/mL). Pooled patient serum was used for the Medium and Low Pools, and stripped serum from Golden West Biologicals, Product #SP1070, was used for the Low Pool. Twenty aliquots from each of the Low, Medium and High Pools were analyzed in a single assay using the LC-MS/MS protocols described in Example 1. The following precision values were determined:

TABLE 2

Intra-Assay Variation: 25-Hydroxyvitamin $D_2$ ($25OHD_2$)

|  | Low 092804-L | Medium 092804-M | High 092804-H |
|---|---|---|---|
| 1 | 26.5 | 46.4 | 103.3 |
| 2 | 23.2 | 51.1 | 96.7 |
| 3 | 23.1 | 52.4 | 107.8 |
| 4 | 21.6 | 50.3 | 104.5 |
| 5 | 26.3 | 47.5 | 96.2 |
| 6 | 25.1 | 54.4 | 98.5 |
| 7 | 25.9 | 54.6 | 100.0 |
| 8 | 21.9 | 50.1 | 110.1 |
| 9 | 23.4 | 50.8 | 97.6 |
| 10 | 23.5 | 53.2 | 105.1 |
| 11 | 22.2 | 52.9 | 105.9 |
| 12 | 24.0 | 54.6 | 94.5 |
| 13 | 26.2 | 49.4 | 93.4 |
| 14 | 24.1 | 59.0 | 113.0 |
| 15 | 25.8 | 52.9 | 112.4 |
| 16 | 23.9 | 59.2 | 113.4 |
| 17 | 29.5 | 52.4 | 107.7 |
| 18 | 24.2 | 50.0 | 115.5 |
| 19 | 19.8 | 53.5 | 114.9 |
| 20 | 26.3 | 60.2 | 126.6 |
| Average (ng/mL) | 24.3 | 52.7 | 105.9 |
| Std Dev | 2.2 | 3.6 | 8.6 |
| CV (%) | 9.0 | 6.9 | 8.1 |

TABLE 3

Intra-Assay Variation: 25-Hydroxyvitamin $D_3$ ($25OHD_3$)

|  | Low 092804-L | Medium 092804-M | High 092804-H |
|---|---|---|---|
| 1 | 22.7 | 43.6 | 99.1 |
| 2 | 22.4 | 45.3 | 93.5 |
| 3 | 22.4 | 50.7 | 98.2 |
| 4 | 21.0 | 40.1 | 95.9 |
| 5 | 21.8 | 41.5 | 82.0 |
| 6 | 20.8 | 42.2 | 97.4 |
| 7 | 22.9 | 50.1 | 96.0 |
| 8 | 19.0 | 42.0 | 106.7 |
| 9 | 21.8 | 44.2 | 96.6 |

TABLE 3-continued

Intra-Assay Variation: 25-Hydroxyvitamin $D_3$ (25OHD$_3$)

| | Low 092804-L | Medium 092804-M | High 092804-H |
|---|---|---|---|
| 10 | 23.4 | 49.5 | 94.9 |
| 11 | 21.8 | 46.5 | 97.9 |
| 12 | 20.7 | 49.9 | 87.1 |
| 13 | 25.4 | 44.7 | 85.5 |
| 14 | 24.5 | 48.0 | 101.5 |
| 15 | 25.1 | 45.8 | 101.5 |
| 16 | 22.5 | 52.0 | 104.7 |
| 17 | 29.2 | 45.9 | 107.7 |
| 18 | 19.5 | 49.3 | 107.6 |
| 19 | 18.1 | 49.6 | 109.4 |
| 20 | 24.8 | 49.3 | 116.1 |
| Average (ng/mL) | 22.5 | 46.5 | 99.0 |
| Std Dev | 2.5 | 3.5 | 8.4 |
| CV (%) | 11.2 | 7.5 | 8.5 |

Each of the Low, Medium and High Pools described above were also analyzed to determine inter-assay precision. Four aliquots from each pool were analyzed over five different assays using the LC-MS/MS protocols described in Example 1. The following precision values were determined:

TABLE 4

Inter-Assay Variation: 25-Hydroxyvitamin $D_2$ (25OHD$_2$)

| | Low 092804-L | Medium 092804-M | High 092804-H |
|---|---|---|---|
| 1 | 26.5 | 46.4 | 103.3 |
| 2 | 23.2 | 51.1 | 96.7 |
| 3 | 23.1 | 52.4 | 107.8 |
| 4 | 21.6 | 50.3 | 104.5 |
| 5 | 26.3 | 47.5 | 96.2 |
| 6 | 25.1 | 54.4 | 98.5 |
| 7 | 25.9 | 54.6 | 100.0 |
| 8 | 21.9 | 50.1 | 110.1 |
| 9 | 23.4 | 50.8 | 97.6 |
| 10 | 23.5 | 53.2 | 105.1 |
| 11 | 22.2 | 52.9 | 105.9 |
| 12 | 24.0 | 54.6 | 94.5 |
| 13 | 26.2 | 49.4 | 93.4 |
| 14 | 24.1 | 59.0 | 113.0 |
| 15 | 25.8 | 52.9 | 112.4 |
| 16 | 23.9 | 59.2 | 113.4 |
| 17 | 29.5 | 52.4 | 107.7 |
| 18 | 24.2 | 50.0 | 115.5 |
| 19 | 19.8 | 53.5 | 114.9 |
| 20 | 26.3 | 60.2 | 126.6 |
| Average (ng/mL) | 24.3 | 52.7 | 105.9 |
| Std Dev | 2.2 | 3.6 | 8.6 |
| CV (%) | 9.0 | 6.9 | 8.1 |

TABLE 5

Inter-Assay Variation: 25-Hydroxyvitamin $D_3$ (25OHD$_3$)

| | Low 092804-L | Medium 092804-M | High 092804-H |
|---|---|---|---|
| 1 | 22.7 | 43.6 | 99.1 |
| 2 | 22.4 | 45.3 | 93.5 |
| 3 | 22.4 | 50.7 | 98.2 |
| 4 | 21.0 | 40.1 | 95.9 |
| 5 | 21.8 | 41.5 | 82.0 |
| 6 | 20.8 | 42.2 | 97.4 |
| 7 | 22.9 | 50.1 | 96.0 |
| 8 | 19.0 | 42.0 | 106.7 |
| 9 | 21.8 | 44.2 | 96.6 |
| 10 | 23.4 | 49.5 | 94.9 |
| 11 | 21.8 | 46.5 | 97.9 |
| 12 | 20.7 | 49.9 | 87.1 |
| 13 | 25.4 | 44.7 | 85.5 |
| 14 | 24.5 | 48.0 | 101.5 |
| 15 | 25.1 | 45.8 | 101.5 |
| 16 | 22.5 | 52.0 | 104.7 |
| 17 | 29.2 | 45.9 | 107.7 |
| 18 | 19.5 | 49.3 | 107.6 |
| 19 | 18.1 | 49.6 | 109.4 |
| 20 | 24.8 | 49.3 | 116.1 |
| Average (ng/mL) | 22.5 | 46.5 | 99.0 |
| Std Dev | 2.5 | 3.5 | 8.4 |
| CV (%) | 11.2 | 7.5 | 8.5 |

Example 3: Analytical Sensitivity: Limit of Detection and Limit of Quantitation Studies To determine the limit of detection of the assay, blank diluent was analyzed 17 times within a single run using the LC-MS/MS protocols described in Example 1. The mean and standard deviation were then calculated. The limit of detection was determined as 2 SD above the mean of the blank peak area ratio based on a back calculation of peak area ratio against the calibration curve. The limits of detection were as follows:

25OHD$_2$: 3.0 ng/mL

25OHD$_3$: 3.5 ng/mL

To determine the limit of quantitation, stock solutions of 25OHD$_2$ and 25OHD$_3$ were used to generate standard curves with the following concentrations: 0, 2, 4, 8, 16, 32, 64 and 128 ng/mL. The diluted samples of the standard curve were analyzed in quadruplicate over five assays using the LC-MS/MS assay described in Example 1. The results of the study were as follows:

TABLE 6

Limit of Quantitation Study Results: 25-Hydroxyvitamin $D_2$ (25OHD$_2$)

| | | #1 | #2 | #3 | #4 | #5 | Summary | |
|---|---|---|---|---|---|---|---|---|
| 0 ng/mL | | −1.2 | −1.3 | −0.5 | −1.2 | −1.1 | Average (ng/mL) | −1.0 |
| | | −1.1 | −1.4 | −0.9 | −1.3 | −0.7 | Standard Deviation | 0.6 |
| | | −1.1 | −1.5 | −0.8 | NA | −2.6 | C of V (%) | 59.0 |
| | | 0.4 | −1.7 | −0.6 | −0.5 | −0.6 | Accuracy (%) | N/A |
| 2 ng/mL | | 3.1 | 2.3 | 2.0 | 2.1 | 3.3 | Average (ng/mL) | 1.9 |
| | | 2.1 | 2.7 | 2.1 | 2.4 | 1.9 | Standard Deviation | 0.6 |
| | | 1.1 | 1.9 | 1.9 | 0.9 | 1.3 | C of V (%) | 33.7 |
| | | 1.2 | 1.1 | 2.1 | 1.8 | 1.4 | Accuracy (%) | 103.9 |

TABLE 6-continued

Limit of Quantitation Study Results: 25-Hydroxyvitamin $D_2$ (25OHD$_2$)

| | #1 | #2 | #3 | #4 | #5 | Summary | |
|---|---|---|---|---|---|---|---|
| 4 ng/mL | 3.5 | 3.9 | 5.0 | 4.5 | 4.8 | Average (ng/mL) | 3.9 |
| | 4.0 | 3.0 | 3.8 | 3.8 | 4.7 | Standard Deviation | 0.7 |
| | 3.6 | 2.9 | 2.8 | 3.1 | 2.0* | C of V (%) | 17.1 |
| | 4.1 | 4.6 | 4.5 | 4.4 | 3.7 | Accuracy (%) | 101.7 |
| 8 ng/mL | 10.2 | 9.1 | 9.1 | 8.8 | 9.8 | Average (ng/mL) | 8.6 |
| | 7.8 | 8.1 | 7.9 | 8.4 | 9.0 | Standard Deviation | 0.8 |
| | 8.6 | 8.3 | 7.4 | 8.4 | 7.5 | C of V (%) | 9.3 |
| | 10.2 | 8.4 | 8.0 | 8.1 | 8.6 | Accuracy (%) | 93.2 |
| 16 ng/mL | 16.0 | 14.8 | 14.4 | 16.7 | 18.3 | Average (ng/mL) | 16.0 |
| | 15.5 | 15.6 | 15.3 | 16.7 | 16.8 | Standard Deviation | 1.1 |
| | 16.6 | 16.7 | 16.8 | 15.8 | 15.2 | C of V (%) | 7.1 |
| | 14.1 | 17.6 | 16.1 | 16.7 | 14.1 | Accuracy (%) | 100.1 |
| 32 ng/mL | 31.3 | 39.9* | 29.9 | 33.2 | 32.7 | Average (ng/mL) | 31.8 |
| | 31.7 | 30.5 | 32.4 | 34.0 | 32.5 | Standard Deviation | 1.9 |
| | 29.5 | 31.2 | 30.2 | 35.7 | 28.7 | C of V (%) | 6.0 |
| | 32.9 | 34.7 | 32.4 | 30.8 | 29.2 | Accuracy (%) | 100.7 |
| 64 ng/mL | 66.5 | 62.2 | 68.5 | 62.6 | 68.8 | Average (ng/mL) | 64.6 |
| | 66.6 | 67.8 | 67.3 | 58.9 | 61.5 | Standard Deviation | 3.2 |
| | 64.4 | 61.4 | 63.7 | 63.5 | 61.3 | C of V (%) | 4.9 |
| | 63.7 | 60.7 | 65.4 | 70.8 | 65.9 | Accuracy (%) | 99.1 |
| 128 ng/mL | 125.1 | 128.2 | 123.4 | 127.8 | 124.1 | Average (ng/mL) | 126.9 |
| | 127.6 | 134.4 | 127.3 | 128.4 | 132.1 | Standard Deviation | 3.5 |
| | 128.9 | 124.5 | 128.5 | 126.5 | 131.7 | C of V (%) | 2.8 |
| | 126.1 | 119.7 | 127.9 | 121.2 | 125.0 | Accuracy (%) | 100.8 |

TABLE 7

Limit of Quantitation Study Results: 25-Hydroxyvitamin $D_3$ (25OHD$_3$)

| | Day #1 (Nov. 19, 2004-1) | Day #2 (Nov. 19, 2004-2) | Day #3 (Nov. 22, 2004-1) | Day #4 (Nov. 23, 2004-1) | Day #5 (Nov. 23, 2004-2) | Summary | |
|---|---|---|---|---|---|---|---|
| 0 ng/mL | −0.5 | −0.9 | −0.3 | 0.2 | −0.6 | Average (ng/mL) | −0.7 |
| | −0.7 | −1.3 | 0.3 | −1.1 | −1.0 | Standard Deviation | 0.6 |
| | 0.0 | −1.0 | −1.1 | −1.3 | 0.6 | C of V (%) | 86.4 |
| | −0.3 | −1.5 | −1.1 | −0.8 | −1.0 | Accuracy (%) | N/A |
| 2 ng/mL | 2.6 | 1.5 | 2.4 | 2.5 | 1.7 | Average (ng/mL) | 1.9 |
| | 1.7 | 0.9 | 3.2 | 2.2 | 1.9 | Standard Deviation | 0.6 |
| | 1.8 | 1.8 | 2.0 | 1.1 | 2.2 | C of V (%) | 31.4 |
| | 1.3 | 2.4 | 1.5 | 1.1 | 2.5 | Accuracy (%) | 104.7 |
| 4 ng/mL | 3.9 | 3.5 | 4.8 | 4.0 | 3.4 | Average (ng/mL) | 3.8 |
| | 3.0 | 4.1 | 3.1 | 3.9 | 3.8 | Standard Deviation | 0.8 |
| | 4.5 | 3.7 | 2.9 | 3.5 | 2.4 | C of V (%) | 19.7 |
| | 4.0 | 5.2 | 3.8 | 3.8 | 5.5 | Accuracy (%) | 104.1 |
| 8 ng/mL | 10.3 | 9.3 | 7.2 | 8.4 | 8.6 | Average (ng/mL) | 8.7 |
| | 10.6 | 8.5 | 7.2 | 10.0 | 9.6 | Standard Deviation | 1.1 |
| | 7.4 | 10.3 | 9.0 | 9.4 | 8.4 | C of V (%) | 13.1 |
| | 9.3 | 7.7 | 8.5 | 7.6 | 6.8 | Accuracy (%) | 91.9 |
| 16 ng/mL | 15.9 | 15.6 | 16.2 | 18.6 | 17.1 | Average (ng/mL) | 16.0 |
| | 13.8 | 16.3 | 14.0 | 17.2 | 15.3 | Standard Deviation | 1.4 |
| | 15.6 | 16.1 | 15.1 | 18.8 | 16.1 | C of V (%) | 8.5 |
| | 14.8 | 17.2 | 17.0 | 14.3 | 15.3 | Accuracy (%) | 99.9 |
| 32 ng/mL | 31.1 | 35.8 | 29.6 | 32.8 | 28.0 | Average (ng/mL) | 31.7 |
| | 30.8 | 29.9 | 31.8 | 33.0 | 32.8 | Standard Deviation | 1.9 |
| | 31.6 | 30.9 | 29.5 | 35.7 | 31.2 | C of V (%) | 6.2 |
| | 31.0 | 34.2 | 31.8 | 30.6 | 31.7 | Accuracy (%) | 101.0 |
| 64 ng/mL | 65.9 | 64.6 | 64.4 | 64.8 | 67.8 | Average (ng/mL) | 64.8 |
| | 67.4 | 62.9 | 62.4 | 60.7 | 57.2 | Standard Deviation | 3.1 |
| | 68.9 | 64.2 | 62.1 | 64.0 | 64.7 | C of V (%) | 4.8 |
| | 63.2 | 64.2 | 66.8 | 67.7 | 71.1 | Accuracy (%) | 98.8 |
| 128 ng/mL | 128.9 | 124.5 | 126.4 | 125.3 | 122.8 | Average (ng/mL) | 127.1 |
| | 129.7 | 135.7 | 128.3 | 125.9 | 128.7 | Standard Deviation | 4.7 |
| | 125.5 | 123.3 | 127.2 | 121.7 | 135.4 | C of V (%) | 3.7 |
| | 121.3 | 121.8 | 137.8 | 121.4 | 124.1 | Accuracy (%) | 100.7 |

Example 4: Assay Reportable Range and Linearity

To establish the linearity of the vitamin D metabolite LC-MS/MS assay, a MultiProbe automated liquid handler robot independently constructed two standard curves by serially diluting a stock solution containing 128 ng/mL 25OHD$_2$ and 128 ng/mL 25OHD$_3$ in 25OHD with a solution of 5% Bovine Serum Albumin Fraction V dissolved in 0.01M PBS. The standard curve samples were analyzed using the LC-MS/MS protocols described in Example 1.

This process routinely produced standard curves with R$^2$ values of 0.99 or higher for each analyte for the range of 4-128 ng/mL.

Figure 2:
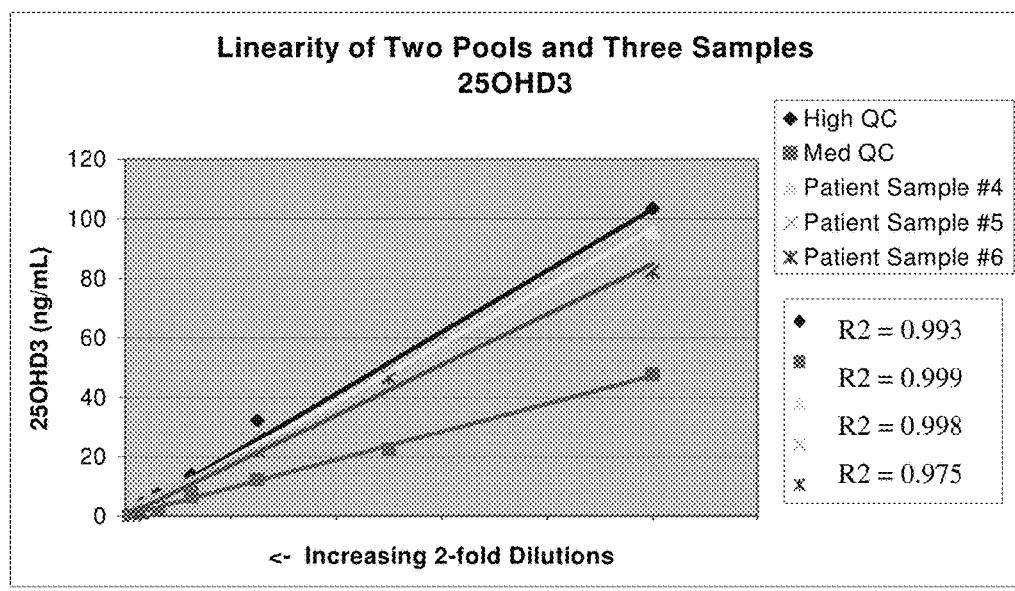
FIG. 2 shows the linearity of the quantification of 25OHD$_3$ in serially diluted stock samples using an LC-MS/MS assay. Details are described in Example 4.

To determine whether patient samples can also be diluted in a linear fashion, a total of eight samples were serially diluted with 25OHD diluent. Two samples were patient pools (Medium and High Control Pools), three were patient samples with high 25OHD$_2$ values and three were patient samples with high 25OHD$_3$ values. All samples were analyzed using the LC-MS/MS protocols described in Example 1. As shown in FIG. 1 and FIG. 2, each sample diluted in a linear fashion (R$^2$>0.98), demonstrating the linear range of the assay.

Figure 3:
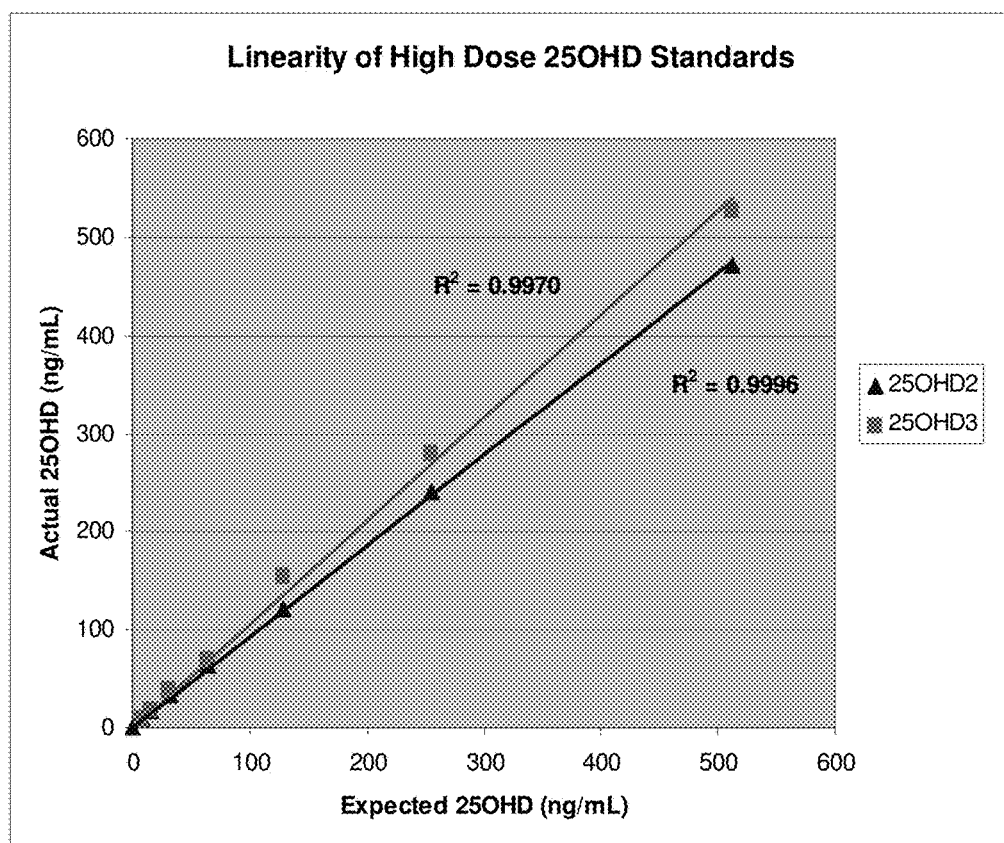
FIG. 3 shows the linearity of the quantification by LC-MS/MS of serially diluted samples containing 25OHD$_2$ and 25OHD$_3$ to final concentrations of 512 ng/mL. Details are described in Example 4.

Additionally, solutions of 25OHD$_2$ and 25OHD$_3$ at 512 ng/mL in 5% Bovine Serum Albumin Fraction V dissolved in 0.01M PBS were prepared and then serially diluted to 8 ng/mL. Each sample was extracted and run in duplicate using the LC-MS/MS protocols described in Example 1. As shown in FIG. 3, each of these curves was linear (R$^2$>0.99).

Example 5: Accuracy of LC-MS/MS Vitamin D Assay

The stock solutions of 25OHD$_2$ and 25OHD$_3$ were quantified based upon the absorbance of the concentrated (10-50 µg/mL) stock solutions in the ultraviolet spectrum. The cis-triene chromophore present in all vitamin D compounds has a peak absorbance of 264 nm, which is dependent upon the analyte concentration. The molar extinction coefficient of 18.3 mM$^{-1}$cm$^{-1}$ was determined using purified, dessicated ergocalciferol and cholecalciferol and was used to determine the concentration of stock solutions for 25OHD$_2$ and 25OHD$_3$.

To determine the ability to recover vitamin D metabolites from spiked serum samples, three patient pools with known levels of 25OHD$_2$, 25OHD$_3$ were spiked with two levels of 25OHD$_2$, 25OHD$_3$ and both 25OHD$_2$ and 25OHD$_3$ together. Each sample was extracted and run in duplicate using the LC-MS/MS protocols described in Example 1. The recovery was calculated by dividing the expected result by the observed result.

TABLE 8

Recovery of 25-hydroxylated vitamin D metabolites from spiked samples.

| | 25OHD$_2$ (ng/mL) | 25OHD$_3$ (ng/mL) | 25OHD$_2$ (% Recovery) | 25OHD$_3$ (% Recovery) |
|---|---|---|---|---|
| Pool#1 | 58 | 51 | — | — |
| Pool#1 + 20 ng/mL 25OHD$_2$ | 75 | 52 | 104 | — |
| Pool#1 + 20 ng/mL 25OHD$_3$ | 52 | 68 | — | 105 |
| Pool#1 + 20 ng/mL of both | 72 | 68 | 109 | 105 |
| Pool#1 + 50 ng/mL 25OHD$_2$ | 104 | 50 | 105 | — |
| Pool#1 + 50 ng/mL 25OHD$_3$ | 56 | 109 | — | 93 |
| Pool#1 + 50 ng/mL of both | 104 | 110 | 104 | 92 |
| Pool#2 | 53 | 47 | — | — |
| Pool#2 + 20 ng/mL 25OHD$_2$ | 76 | 51 | 97 | — |
| Pool#2 + 20 ng/mL 25OHD$_3$ | 52 | 66 | — | 101 |
| Pool#2 + 20 ng/mL of both | 70 | 65 | 105 | 103 |
| Pool#2 + 50 ng/mL 25OHD$_2$ | 107 | 53 | 96 | — |
| Pool#2 + 50 ng/mL 25OHD$_3$ | 57 | 109 | — | 88 |
| Pool#2 + 50 ng/mL of both | 100 | 105 | 103 | 92 |
| Pool#3 | 53 | 47 | — | — |
| Pool#3 + 20 ng/mL 25OHD$_2$ | 69 | 44 | 106 | — |
| Pool#3 + 20 ng/mL 25OHD$_3$ | 55 | 75 | — | 90 |
| Pool#3 + 20 ng/mL of both | 74 | 69 | 98 | 97 |
| Pool#3 + 50 ng/mL 25OHD$_2$ | 96 | 48 | 107 | — |
| Pool#3 + 50 ng/mL 25OHD$_3$ | 53 | 114 | — | 85 |
| Pool#3 + 50 ng/mL of both | 105 | 113 | 98 | 85 |

Figure 4:
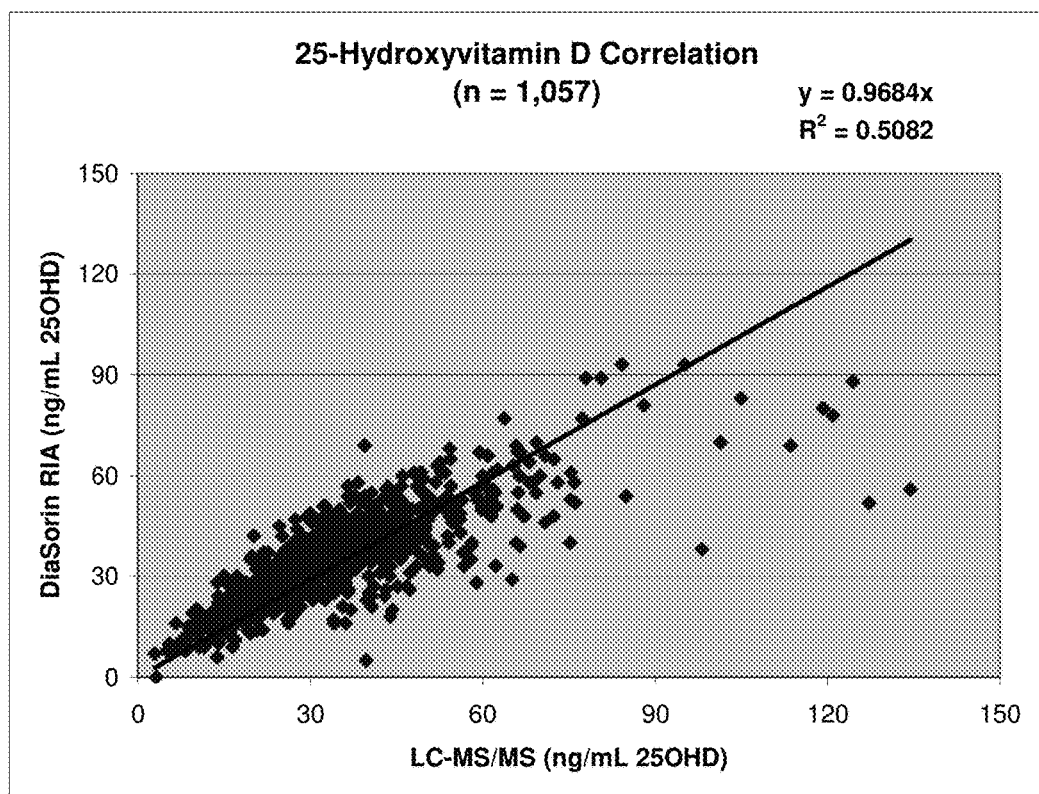
FIG. 4 shows the correlation between detection of total 25-hydroxyvitamin D using an LC-MS/MS assay and a commercially available radioimmunoassay kit. Details are described in Example 6.

Example 6: Comparison LC-MS/MS Vitamin D Metabolite Assay and RIA Procedures A total of 1,057 patient samples were assayed using the LC-MS/MS methods described in Example 1 and a vitamin D radioimmunoassay commercially available from DiaSorin. FIG. 4 shows the correlation between detection of total 25-hydroxyvitamin D using the LC-MS/MS assay and a commercially available radioimmunoassay kit; the R$^2$ value was 0.5082 with a slope of 0.9684.

Example 7: Selectivity of the LC-MS/MS Assay

Samples containing various commercially available vitamin D metabolites and analogues at a concentration of 100 ng/mL were prepared. The samples were extracted and run in duplicate using the LC-MS/MS methods described in Example 1. None of the tested compounds exhibited detectable cross reactivity in the 25OHD$_2$ and 25OHD$_3$ assays.

TABLE 9

Cross-Reactivity of the LC-MS/MS method with various vitamin D analogues and metabolites.

| | Compound Mass (Da) | Cross-Reactivity (25OHD$_2$) | Cross-Reactivity (25OHD$_3$) |
|---|---|---|---|
| 25-Hydroxyvitamin D$_2$ (25OHD$_2$) | 412 | (100%) | ND |

TABLE 9-continued

Cross-Reactivity of the LC-MS/MS method with various vitamin D analogues and metabolites.

| | Compound Mass (Da) | Cross-Reactivity (25OHD$_2$) | Cross-Reactivity (25OHD$_3$) |
|---|---|---|---|
| 25-Hydroxyvitamin D$_3$ (25OHD$_3$) | 400 | ND | (100%) |
| Internal Standard ($^6$D-25OHD$_3$) | 406 | ND | ND |
| Vitamin D$_2$ (Ergocalciferol) | 396 | ND | ND |
| Vitamin D$_3$ (Cholecalciferol) | 384 | ND | ND |
| 1α,25(OH)$_2$D$_2$ | 428 | ND | ND |
| 1α,25(OH)$_2$D$_3$ | 416 | ND | ND |
| 25,26(OH)$_2$D$_3$ | 416 | ND | ND |
| 1α(OH)D$_2$ (Doxercalciferol) | 412 | ND | ND |
| 1α(OH)D$_3$ (Alfacalcidiol) | 400 | ND | ND |

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A method for determining the amount of a vitamin D metabolite in a sample by tandem mass spectrometry, comprising:
   (a) generating a protonated and dehydrated precursor ion of said vitamin D metabolite by atmospheric pressure chemical ionization (APCI);
   (b) generating one or more fragment ions of said precursor ion; and
   (c) detecting the amount of one or more of said ions generated in step (a) or (b) or both and relating the detected ions to the presence or amount of said vitamin D metabolite in said sample;
   wherein said vitamin D metabolite is 25-hydroxyvitamin D$_3$ or 25-hydroxyvitamin D$_2$.

2. The method of claim 1, wherein said sample is subjected to a purification step prior to ionization step (a).

3. The method of claim 2, wherein said purification step comprises liquid chromatography.

4. The method of claim 3, wherein said liquid chromatography comprises high performance liquid chromatography (HPLC).

5. The method of claim 2, wherein said purification step comprises protein precipitation.

6. The method of claim 5, wherein said purification step does not include high turbulence liquid chromatography (HTLC).

7. The method of claim 2, wherein said purification step comprises chiral chromatography.

8. The method of claim 1, wherein said vitamin D metabolite is 25-hydroxyvitamin D$_3$.

9. The method of claim 1, wherein said vitamin D metabolite is 25-hydroxyvitamin D$_2$.

10. A method for determining the amount of 25-hydroxyvitamin D$_3$ and 25-hydroxyvitamin D$_2$ in a sample in a single assay, said method comprising:
    (a) ionizing by atmospheric pressure chemical ionization (APCI) said 25-hydroxyvitamin D$_3$ and 25-hydroxyvitamin D$_2$ to generate protonated and dehydrated precursor ions specific for each of said 25-hydroxyvitamin D$_3$ and 25-hydroxyvitamin D$_2$;
    (b) generating one or more fragment ions of each of said precursor ions; and
    (c) detecting the amount of one or more of said ions generated in step (a) or (b) or both and relating the detected ions to the amount of 25-hydroxyvitamin D$_3$ and 25-hydroxyvitamin D$_2$ in said sample.

11. The method of claim 10, wherein said sample subjected to a purification step prior to said ionization step (a).

12. The method of claim 11, wherein said purification step comprises liquid chromatography.

13. The method of claim 12, wherein said liquid chromatography comprises high performance liquid chromatography (HPLC).

14. The method of claim 11, wherein said purification step comprises protein precipitation and does not include high turbulence liquid chromatography.

15. The method of claim 10, wherein said sample comprises a biological sample.

16. The method of claim 10, wherein said sample comprises plasma or serum.

* * * * *